US008916387B2

(12) United States Patent
Nilsson et al.

(10) Patent No.: US 8,916,387 B2
(45) Date of Patent: Dec. 23, 2014

(54) DIAGNOSIS AND TREATMENT OF ALZHEIMER'S DISEASE

(76) Inventors: Jonas Nilsson, Hisings-Backa (SE); Adnan Halim, Malmö (SE); Göran Larson, Göteborg (SE); Kaj Blennow, Göteborg (SE); Gunnar Brinkmalm, Mölndal (SE); Erik Portelius, Hyssna (SE); Henrik Zetterberg, Mölnlycke (SE)

( * ) Notice: Subject to any disclaimer, the term of this patent is extended or adjusted under 35 U.S.C. 154(b) by 0 days.

(21) Appl. No.: 13/881,387

(22) PCT Filed: Oct. 28, 2011

(86) PCT No.: PCT/EP2011/069006
§ 371 (c)(1),
(2), (4) Date: Apr. 25, 2013

(87) PCT Pub. No.: WO2012/056008
PCT Pub. Date: May 3, 2012

(65) Prior Publication Data
US 2014/0037658 A1    Feb. 6, 2014

Related U.S. Application Data

(60) Provisional application No. 61/455,891, filed on Oct. 28, 2010.

(51) Int. Cl.
*G01N 24/00* (2006.01)
*G01N 24/14* (2006.01)
*G01N 33/68* (2006.01)
*H01J 49/00* (2006.01)
*A61K 39/00* (2006.01)

(52) U.S. Cl.
CPC ........ *G01N 33/6896* (2013.01); *H01J 49/0027* (2013.01); *G01N 2333/4709* (2013.01); *A61K 39/0007* (2013.01); *G01N 2800/2821* (2013.01)
USPC ...... 436/173; 530/413; 530/417; 250/339.07; 250/339.08

(58) Field of Classification Search
CPC .......... G01N 2400/02; G01N 2800/50; G01N 2800/2821; G01N 2800/28; G01N 2800/2814; G01N 33/6896; G01N 2400/38
See application file for complete search history.

(56) References Cited

U.S. PATENT DOCUMENTS 5,461,143 A   10/1995   Wong
6,410,598 B1   6/2002   Vitek

FOREIGN PATENT DOCUMENTS

WO   WO 02/15721 A2   2/2002

OTHER PUBLICATIONS

Horikoshi Y et al. (2004) Development of Abeta terminal end-specific antibodies and sensitive ELISA for Abeta variant. Biochem. Biophys. Res. Comm. 319:733-737.*
Kuby J, editor. Immunology, Third Edition, 1997, pp. 131-134.*
Lefebvre T et al. (2005) Does O-GlcNAc play a role in neurodegenerative diseases? Expert Rev. Proteomics, 2(2):265-275.*
Miyazaki H et al. (1996) Differential effects of a murine monoclonal antibody reactive with the disialylgalactosyl residue on the growth of melanoma cells and T cell activation: Comparison with anti-GD3 antibody R24. Int. J. Oncol. 9:241-245.*
Northstar BioProducts memorandum, Sep. 15, 2011.*
Terryberry et al. (1998) Neurobiology Aging, 19(3):205-216.*
Halim, A. et al., 2011, Site-specific characerization of threonine, serine, and tyrosine glycosylations of amyloid precursor . . . , Proc. Natl. Acad. Sci. USA (2011) 29:11848-53.
Perdivara, I. et al., 2009, Elucidation of O-glycosylation structures of the beta-amyloid precursor protein by liquid . . . , J. Proteome Res. 8(2):631-642.
Zimmerman, M. et al., 2004, Acetylcholinesterase inhibitors increase ADAM10 activity by promoting its trafficking . . . , J. Neurochemistry 90: 1489-99.

* cited by examiner

*Primary Examiner* — Kimberly A Ballard
(74) *Attorney, Agent, or Firm* — Lynn E. Barber

(57) ABSTRACT

Methods are provided for the prevention, treatment and diagnosis of Alzheimer's disease, based on the glycosylation pattern of amyloid-beta peptides in body fluids and tissues.

9 Claims, 1 Drawing Sheet

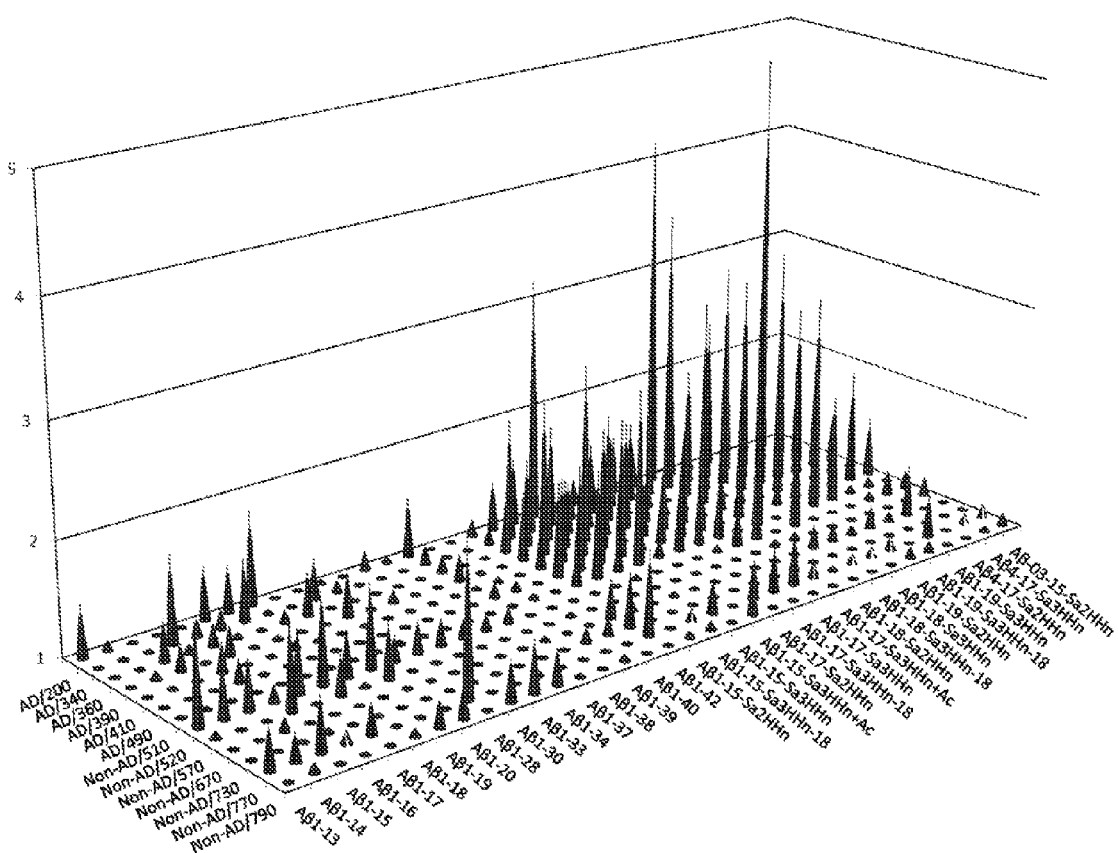

```
                        SEQUENCE LISTING

<160> NUMBER OF SEQ ID NOS: 8

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 15
<212> TYPE: PRT
<213> ORGANISM: Homo sapiens

<400> SEQUENCE: 2

Asp Ala Glu Phe Arg His Asp Ser Gly Tyr Glu Val His His Gln
1               5                   10                  15

<210> SEQ ID NO 3
<211> LENGTH: 40
<212> TYPE: PRT
<213> ORGANISM: Homo sapiens

<400> SEQUENCE: 3

Asp Arg Gly Leu Thr Thr Arg Pro Gly Ser Gly Leu Thr Asn Ile Lys
1               5                   10                  15

Thr Glu Glu Ile Ser Glu Val Lys Met Asp Ala Glu Phe Arg His Asp
            20                  25                  30

Ser Gly Tyr Glu Val His His Gln
        35                  40

<210> SEQ ID NO 4
<211> LENGTH: 20
<212> TYPE: PRT
<213> ORGANISM: Homo sapiens

<400> SEQUENCE: 4

Asp Ala Glu Phe Arg His Asp Ser Gly Tyr Glu Val His His Gln Lys
```

```
1               5              10             15
Leu Val Phe Phe
            20

<210> SEQ ID NO 5
<211> LENGTH: 6
<212> TYPE: PRT
<213> ORGANISM: Homo sapiens

<400> SEQUENCE: 5

Tyr Glu Val His His Gln
1               5

<210> SEQ ID NO 6
<211> LENGTH: 9
<212> TYPE: PRT
<213> ORGANISM: Homo sapiens

<400> SEQUENCE: 6

His Asp Ser Gly Tyr Glu Val His His
1               5

<210> SEQ ID NO 7
<211> LENGTH: 7
<212> TYPE: PRT
<213> ORGANISM: Homo sapiens

<400> SEQUENCE: 7

Asp Ser Gly Tyr Glu Val His
1               5

<210> SEQ ID NO 8
<211> LENGTH: 6
<212> TYPE: PRT
<213> ORGANISM: Homo sapiens

<400> SEQUENCE: 8

Phe Arg His Asp Ser Gly
1               5
```

DIAGNOSIS AND TREATMENT OF ALZHEIMER'S DISEASE

FIELD OF THE INVENTION

The present invention relates generally to medicine. More specifically the invention relates to the prevention, treatment and diagnosis of Alzheimer's disease, employing the novel finding that Alzheimer's disease is correlated with an O-glycosylation of a tyrosine residue on amyloid-beta peptides.

BACKGROUND OF THE INVENTION

Alzheimer's disease (AD), first described by the Bavarian psychiatrist Alois Alzheimer in 1907, is a progressive neuropsychiatric disorder which begins with short term memory loss and proceeds to loss of cognitive functions, disorientation, impairment of judgment and reasoning and, ultimately, dementia. AD is the most common form of dementia. AD has been estimated to afflict 5 to 11 percent of the population over age 65 and as much as 47 percent of the population over age 85. Moreover, as adults born during the population boom of the 1940's and 1950's approach the age when AD becomes more prevalent, the control and treatment of AD will become an even more significant health care problem.

Cortical atrophy, neuronal loss, region-specific amyloid deposition, neuritic plaques, and neurofibrillary tangles are key neuropathological features in the AD brain. These alterations are thought to be linked to cognitive decline, which clinically defines AD.

The major constituent of the neuritic plaque, beta-amyloid peptides (Abeta), arises from proteolytic cleavage of a larger precursor protein, the amyloid precursor protein (APP) (Kang, et al., 1987; Tanzi, et al., 1987). Abeta is produced by normal cells and can be detected as circulating peptides in the plasma and cerebrospinal fluid (CSF) of healthy humans. APP is a ubiquitously expressed transmembrane glycoprotein, which undergoes proteolysis by several secretases in the processes of ectodomain shedding and regulated intramembrane proteolysis (Wolfe, Curr Top Dev Biol 2003). In the amyloidogenic pathway beta- and gamma-secretases cleave APP into several Abeta isoforms of which Abeta1-42 is regarded to have a direct link to AD since it is a major constituent of extracellular amyloid deposits in the brains of AD patients, and has been shown to be synaptotoxic. APP may also be cleaved in the middle of the Abeta1-42 sequence by alpha-secretase, precluding the formation of full length Abeta and considered to protect from amyloid deposition in the brain (Blennow et al, Nat Rev Neurol 2010, Haass et al, Nat Rev Mol Cell Biol 2007). The alpha-secretase will thus cleave the membrane glycoprotein APP such that the Abeta1-42 is not produced, thus eliminating a harmful amyloidogenic peptide. There might be a very delicate and not well understood balance between the alpha- and gamma-secretases in this membrane close environment and glycosylation may favor alpha-cleavage. The shorter products when produced from the alpha-secretase cleavage, like the Abeta1-16, and most likely the glyco-Abeta 1-X series of glycopeptides could all interfere with the deposition process—but how such a protective effect would work is not know; interfering with a spontaneous aggregation, or with a facilitator in solution or close to or associated with the membrane. Also, clearance of formed amyloidegenic Abeta 1-42 by the action of several peptidases, including neprilysin and insulin degrading enzyme, is believed to counteract amyloid build-up. In general, the proteolytic destiny and half-life of proteins may not only be governed by primary sequences and the availability of proteases, but also by post-translational modifications such as glycosylations, which may block a protease from accessing its target proteolytic site. This has been described for a few proteins (Marinaro et al, Eur J Biochem 2000, Semenov et al, Clin Chem 2009, Gram Schjoldager K T et al., J Biol Chem 2010).

A biomarker is an objective measure of a biological or pathogenic process that can be used to evaluate disease risk or prognosis, to guide clinical diagnosis, or to monitor therapeutic interventions. Since the CSF is in direct contact with the extracellular space of the brain, biochemical changes in the brain are reflected in the CSF. Today, there are three CSF biomarkers for AD that have been evaluated in numerous studies, showing a diagnostic accuracy of 80-85% (Blennow et al. Nat Rev Neurol 2010; 6:131-144). Since this figure is too low for such a common and severe disease as AD there is a need for additional biomarkers that will improve the diagnostic performance. Further, a biomarker should reflect a specific pathogenic process of the disease.

As AD is a growing social and medical problem, there is a strong need for sensitive and specific methods for early diagnosing or prognosing said disease in subjects as well as for introduction of new methods of treatment.

There is currently no treatment for AD that can reverse or slow down the disease progression. AD represents a major health problem and an effective drug treatment of the disease would represent a major breakthrough.

Thus it was an object of the invention to provide new ways of diagnosing, prognosing, preventing and treating AD.

SUMMARY OF THE INVENTION

Tyr10 glycosylated Abeta has a large potential as biomarker for AD since it allows measurement of a novel specific molecular mechanism linked to the disease. Tyr10 glycosylated Abeta may thus be valuable as biomarker both for diagnosis, to predict progression, to monitor treatment effects, and to study disease pathogenesis directly in man.

The invention relates in one aspect to an in vitro method for diagnosing or prognosing Alzheimer's disease in a subject, or determining whether a subject is at increased risk of developing Alzheimer's disease, comprising: a. determining the amounts of Abeta peptide with O-linked Tyr10 glycosylation in a sample; and b. comparing said level to a reference value representing a known disease or health status, wherein a varied level in said sample relative to a said reference value representing a known health status indicates a diagnosis, or prognosis, or increased risk of Alzheimer's disease. The invention relates in one aspect to methods to analyze the extent of O-glycosylation at Tyr10 of Abeta for diagnostic and prognostic purposes for Alzheimer's disease (AD).

The invention relates in another aspect to products for analysis of O-glycosylation at Tyr10 of Abeta for diagnostic and prognostic purposes for AD.

The invention relates in another aspect to modulation of the O-glycosylation at Tyr10 of Abeta for therapeutic purposes in AD.

Another aspect is to use screening methods to find molecules that modulate the O-glycosylation at Tyr10 of Abeta for therapeutic and preventive purposes in AD.

Another aspect is to provide products for the modulation of O-glycosylation at Tyr10 of Abeta to be used against AD.

Another aspect of the invention is to prevent AD by modulating the O-glycosylation at Tyr10 of Abeta.

Another aspect of the invention is the use of Abeta peptides with Tyr10 glycosylation to prevent and/or treat AD by modulating the interaction between endogenous Abeta and proteases.

Another aspect of the invention is the use of Abeta peptides to modulate in vivo Tyr10 glycosylation in order to prevent and/or treat AD.

Other objects and advantages of the present invention will become obvious to the reader and it is intended that these objects and advantages are within the scope of the present invention.

BRIEF DESCRIPTION OF THE DRAWINGS

FIG. 1 shows an intensity ratio map for the relative concentrations of individual Abeta peptides and glycopeptides for AD patients versus controls

DEFINITIONS

The term O-linked glycan and glycosylation are used interchangeably.

The term "antibody" includes monoclonal antibodies and polyclonal antibodies as well as other immunoglobulin-based recognition molecules such as single chain antibodies, F(ab')$_2$ fragments and Fab' fragments The term "antibody-like" refers to molecules with antigen-specific binding, such as affibodies, affilins, anticalins, monobodies etc.

The term glycan and glycosylation are used interchangeably and refer to the carbohydrate moiety present on Tyr10 of Abeta. The terms sialylation and sialylated are used to describe the presence of sialic acid (Neu5Ac) in the described glycans.

The level of glycosylation at Tyr10 of Abeta and relative abundance of glycosylated Tyr10 are based on measured signals corresponding to the amount of Tyr10 glycosylated Abeta in a sample, which may or may not be given in relation to the measured signal from unglycosylated Abeta peptide.

The term "diagnosis" also includes prognosis.

The term "detection moieties" includes detectable labels conjugated to a binding moiety with affinity for the detection ligand, a detection ligand or present in the physical surrounding of the binding moiety (e.g. in lipid vesicles).

The term "treating" includes both curative and ameliorative treatment.

The term "Abeta peptide" refers to proteolytic fragments of APP, and may be glycosylated or non-glycosylated. The term "Abeta glycopeptide" refers to glycosylated Abeta peptides. They may be glycosylated at one or more sites. The Abeta glycopeptide may be glycosylated at Tyr10 (Abeta numbering).

The term "Mild Cognitive Impairment" (MIC) is a clinical diagnosis, which is a milder reduction in cognitive capacity without dementia.

The term "Cognitive Impairment" refers to a symptom which may also include dementia.

DETAILED DESCRIPTION OF THE INVENTION

The invention relates in one aspect to Abeta peptides 1-X and Abeta glycopeptides 1-X. We immunopurified Abeta peptides and glycopeptides using the 6E10 antibody (Abeta epitope; F$^4$RHDSG$^9$, Signet Laboratories, Inc., Dedham, Mass., USA), which recognizes amino acid residues ~4-9 of the Abeta sequence (in the following text referred to as Abeta numbering). The Abeta sequence of APP is here defined as starting with Asp672 of the human APP-770 isoform (A4_HUMAN or P05067 in the Uniprot protein database). The same Abeta sequence is equally part of other APP isoforms including, but not limited to, APP-695 and APP-751. The Abeta 1-42 peptide sequence is thus DAEFRHDS-GYEVHHQKLVFFAEDVGSNKGAIIGLMVGGVVIA (SEQ ID NO. 1); the Abeta 1-15 sequence is DAEFRHDS-GYEVHHQ (SEQ ID NO. 2); and the APP/Abeta-25-15 peptide sequence is DRGLTTRPGSGLTNIKTEEISEVKM-DAEFRHDSGYEVHHQ (SEQ ID NO. 3). Met671 of the human APP-770 isoform is thus Met(−1) in relation to the Abeta sequence. Many residues of the Abeta sequence may differ between different organisms or may be switched at will to others in the course of experiments, but the amino acid sequence homology of the peptides of the invention may be 50% to 100% to that of the human sequence, as determined by the use of Basic Local Alignment Search Tool (BLAST), which will make it identifiable as the Abeta sequence. The homology may for example be 50 to 100%, such as 60, 65, 70, 75, 80, 85, 90, 92, 95, 96, 97, 98, 99 or 100% homology with the human Abeta sequence. In other embodiments the homology of the peptide may be for example 50 to 98%, or for example from 60 to 98%, or for example from 70 to 99%, or for example from 80 to 99%, or for example from 85 to 99%, or for example from 89 to 99%, or for example from 95% to 99% homologous with the human Abeta sequence. In one embodiment the peptide of the invention comprises at least the sequence DSGYEVH (SEQ ID NO 7), such as a peptide Abeta 1-15 (SEQ ID NO:2), such as a peptide Abeta-25-15 (SEQ ID NO. 3).

Also, the Abeta peptide of the invention may be chemically modified or derivatized on any of the amino acid residues. This includes the modification of e.g. the N-terminal and/or the C-terminal of the Abeta peptide sequence with chemical groups, or the elongation with any peptide sequence, but also deletions and insertions or other modifications of any of the amino acids (including Tyrosine 10) of the Abeta peptides.

The invention also relates to APP and/or Abeta peptides of the invention which are glycosylated on Tyrosine 10 (Tyr10). We detected several long APP/Abeta glycopeptides (see Table 2) for instance APP/Abeta-25-15 (SEQ ID NO. 3), -51-15 and -57-15, which all ended with residue 15 of the Abeta sequence (-X-15 series, Abeta numbering) and had masses including 1-5 sialylated O-glycans within the sequence. In addition, several truncated Abeta peptides such as Abeta1-20 (DAEFRHDSGYEVHHQKLVFF, SEQ ID NO. 4), 1-19, 1-18, 1-17 and 1-15 (Abeta 1-X series), as well as Abeta-3-15, 4-15 and 4-17, were identified with mass and structure corresponding to one Neu5AcHex(Neu5Ac)Hex-NAc-O— glycan within each peptide. Since the Abeta 1-20 sequence only contains one possible O-glycosylation site (Ser8) we initially took it for granted that Ser8 was the glycosylation site. This conclusion was based on the common knowledge that O-glycans with Neu5Ac-Hex-HexNAc-O— structure (only presently known to be compatible with Neu5Ac-Gal-GalNAc-O— composition) are known to be glycosidically attached only to serine or threonine residues in proteins. This type of O-glycosylation is sometimes known as mucin-like glycosylation. We wrote an abstract regarding the possible Ser8 glycosylation of Abeta 1-X peptides and presented them on a poster at the 9th European FTMS Workshop, 6-9 Apr. 2010, Lausanne, Switzerland. After this conference we performed additional experiments using Electron capture dissociation (ECD) fragmentation of Abeta glycopeptides in the mass spectrometer to verify the peptide sequences. In ECD the peptide backbone is fragmented in the presence of intact glycans, which can be used to pinpoint glycosylation sites within O-glycosylated peptides that contain several possible serine and/or threonine attachment sites.

To our surprise we unexpectedly found that Tyr10 (Abeta numbering) was the glycosylation site for the Abeta 1-X glycopeptides. Tyrosine residues in proteins are previously known to sometimes be post translationally modified by sulfation, phosphorylation, nitration, glucosylation (in the glucose chain of glycogenin in glycogen). Furthermore, complex glycosylations on tyrosine can be found in a few bacterial capsular proteins (Zarschler et al, Glycobiology 2010). However, this is the first time a mammalian protein has been identified with a sialylated glycan on a tyrosine residue and the first time a HexNAc residue has been found in a glycosidic linkage to a tyrosine residue. Sialic acids are commonly found both on N-glycans and O-glycans and are typically found attached to the outermost (non-reducing) ends of glycan chains on extracellular proteins. The sialic acids function as recognition elements and binders between the glycoprotein and its interacting partners in a range of biological processes.

Without wishing to be bound by theory, it is reasonable to believe that a large (~1 kDa) and negatively charged glycan on Tyr10 (Abeta numbering) may substantially influence the mode upon which this region of APP can interact with the membrane. We propose that the conformational (or structural) change of APP induced by the presence of a Tyr10 O-glycosylation (Abeta numbering) will affect gamma-secretase cleavage of APP at positions 40-42 (Abeta numbering), so that it is switched such that the residues at positions 17-20 become the preferred cleavage sites. We also propose that, as an alternative, the conformational (or structural) change of APP induced by the presence of a Tyr10 O-glycosylation (Abeta numbering) will affect cleavage of APP by the enzyme (or enzymes) called alpha-secretase (or secretases), so that it changes the preference for cleavage at positions 15-20 (Abeta numbering). As a third possibility, we propose that the presence of a Tyr10 O-glycosylation (Abeta numbering) will affect cleavage of APP by the enzyme (or enzymes) called beta-secretase (or secretases, including BACE1, BACE2 and cathepsin B), so that it changes the preference for cleavage at positions 1 and/or 4 and/or 10 and/or 19 and/or 34 (Abeta numbering) in the Abeta sequence. Also, the positioning of a glycan at Tyr10 will be able to block other proteases from cleaving the Abeta sequence, and will modulate which proteolytic end products that will finally appear. Additionally we propose that Tyr10 O-glycosylation (Abeta numbering) will block nitration of this tyrosine residue in APP and Abeta peptides.

Interestingly, we found that the relative abundance of Tyr10 glycosylated Abeta peptides versus unglycosylated Abeta peptides (excluding Abeta 1-42 which is known to be markedly reduced in AD) was markedly elevated in CSF in AD patients compared to matched controls (FIG. 1). The corresponding unglycosylated peptides did not display this difference in CSF between AD patients and non-AD controls. The controls were patients with dementia not diagnosed as AD.

Glycosylation of APP at Tyr10 (Abeta numbering) may limit the beta-secretase induced cleavage at Asp1 to produce Alzheimer-associated aggregation-prone Abeta1-42 and other long Abeta peptides. Modulation of this APP/Abeta glycosylation therefore represents an interesting therapeutic target.

In the present invention, we thus describe the use of attachment site-specific structures of O-linked glycans, including a novel tyrosine glycosylation, that are positioned in vicinity of proteolytic sites on the Abeta peptide sequence, in diagnosis and treatment of AD. Thus the invention relates to the use of the glycan structure present on Tyr10 in Tyr10 glycosylated Abeta glycopeptide and/or APP in medicine, diagnosis or prognosis. The present invention also relates to the use of the invented Abeta peptides 1-X, Tyr10 glycosylated Abeta glycopeptides 1-X, Tyr10 glycosylated APP, or combinations thereof in medicine, diagnosis or prognosis.

The use according to the invention in medicine, or for diagnosis or prognosis wherein the disease may be one in which amyloid beta deposit is implicated, such as for example cerebral amyloid angiopathy and/or Alzheimer's disease and/or HIV associated neurocognitive disorders (HAND).

Tyrosine 10 (Tyr10) is defined as Tyr10 according to the numbering of Abeta. Glycosylation on Tyr10 of APP (Abeta numbering) and/or Tyr10 of Abeta can be used for diagnosis in several different contexts. These include, but are not limited to, as a diagnostic marker (a marker used to make, or assist to make, the diagnosis of AD), a risk marker (a marker to establish or determine the risk to develop AD), a prognostic marker (a marker to predict the prognosis or clinical progression rate of AD), a therapeutic marker (a marker to identify and/or monitor the biochemical effect of a drug or a drug candidate) and a surrogate marker (a marker to predict the clinical outcome of a drug or a treatment intervention). The diagnosis may also be for a disease wherein amyloid beta deposit is implicated, such as for example cerebral amyloid angiopathy, HAND and/or Alzheimer's disease.

In the present invention we use the unexpected finding of a sialylated glycan attached to Tyr10 of the Abeta sequence for diagnosis, prevention and treatment of AD. Thus, we take advantage of knowledge of and structural as well as physicochemical and immunogenic characteristics of both the peptide part and the carbohydrate part of the Tyr10 glycosylated Abeta peptides. The O-linked sialylated glycan on Tyr10 had the following carbohydrate structures: NeuAc-Hex-HexNAc-O-Tyr10; NeuAc-Hex-(NeuAc)-HexNAc-O-Tyr10; NeuAc-NeuAc-Hex-(NeuAc)-HexNAc-O-Tyr10; O-Acetyl-NeuAc-NeuAc-Hex-(NeuAc)-HexNAc-O-Tyr10; and lactonized NeuAc-NeuAc-Hex-(NeuAc)-HexNAc-O-Tyr10, where NeuAc is N-acetylneuraminic acid, also known as sialic acid, where Hex is a hexose which has e.g. galactose, glucose or mannose structure; where HexNAc is N-acetylhexosamine which has e.g. N-acetylgalactosamine, N-acetylglucosamine or N-acetylmannosamine structures. For lactonized NeuAc-NeuAc-Hex-(NeuAc)-HexNAc-O-Tyr10 the two terminal sialic acids have formed an intramolecular lactone (ester bond) and expelled water. For O-AcetylNeuAc a second acetyl group was attached to a free hydroxyl of the terminal sialic acid. The glycan may however have a different structure when studied in other samples or in cell cultures. For instance, sometimes terminating sialic acids may be lacking. In other instances, the sialic acids may be elongated into long chains of sialic acids, so called polysialic acid. The existence of polysialic acid on Tyr 10 of Abeta from human CSF samples cannot be excluded. The glycan will however in all cases be attached to Tyr10 of the Abeta sequence. Hereinafter these glycan structures attached to Tyr10 of the Abeta sequence are those described for the Tyr10 glycosylations.

The invention further relates to the use of one or more of Tyr10 glycosylated Abeta 1-X peptides, Tyr10 glycosylated APP, the Tyr10 glycosylation structure or combinations thereof for generating antibodies or antibody-like molecules. The antibodies or antibody-like molecules of the invention may be generated by any method. Methods of generating antibodies or antibody-like molecules are known in the art. The invention further relates to the antibodies and antibody-like molecules thus generated.

The invention further relates to antibodies raised against Abeta peptides 1-X, Tyr10 glycosylated Abeta 1-X, and/or APP glycosylated on Tyr10. One example of an epitope useful for establishing antibodies towards the Tyr10 glycosylated Abeta glycopeptides, for example against Tyr10 glycosylated Abeta 1-15, is the Tyr10 glycosylated peptide HDSGYEVHH (SEQ ID NO:6). A further example may be Tyr10 glycosylated peptide DSGYEVH (SEQ ID NO 7) where Y is Tyr681 of the isoform APP770 combined with the minimal glycan epitope of Tyr10 glycosylated Amyloid beta 1-15; i.e. Neu5Acalpha2,6HexNAc-O-Tyr or HexNAc-O-Tyr where HexNAc may be GalNAc, GlcNAc (or ManNAc) and the glycosidic link either alpha or beta from C1 of the inner monosaccharide. Changes (substitutions, deletions or insertions) of single amino acid residues in the Abeta peptide or glycopeptide sequence or derivatizations and conjugations of single amino acids in the Abeta 1-15 sequence, specifically in the N- and/or C-terminal ends, may be introduced to increase the immune response or to reflect alterations found in vivo. The amino acid sequence homology of the peptide used to raise the antibody of the invention may have 50% to 100% homology to that of the human sequence, as determined by the use of Basic Local Alignment Search Tool (BLAST). The homology may for example be 50 to 100%, %, such as 60, 65, 70, 75, 80, 85, 90, 92, 95, 96, 97, 98, 99 or 100% homology with the human Abeta sequence. The peptide used to raise the antibody may for example be 70% identical to the Amyloid beta sequence stored in reference protein databases (e.g. Uniprot).

The invention further relates to antibodies or antibody-like molecules against the Tyr10 glycosylation of Tyr10 glycosylated Abeta glycopeptides.

Thus the invention relates in one aspect to a Tyr10 glycosylated Abeta peptide, for example wherein said peptide comprising at least the sequence Tyr10 glycosylated [DSGYEVH (SEQ ID NO 7)]. In one embodiment the invention relates to a Tyr10 glycosylated Abeta peptide selected from the group consisting of Tyr10 glycosylated Abeta 1-X, Tyr10 glycosylated Abeta 1-15, and Tyr10 glycosylated Abeta-24-15 Tyr10 glycosylated peptide HDSGYEVHH, Tyr10 glycosylated peptide DSGYEVH (SEQ ID NO 7), or Tyrposine glycosylated with Neu5Acalpha2,6HexNAc-O-Tyr or HexNAc-O-Tyr where HexNAc may be GalNAc, GlcNAc (or ManNAc)

In further embodiments the invention relates to a composition comprising the peptide of the invention and one or more pharmaceutically acceptable carriers. In further embodiments the invention relates to an antibody or antibody-like molecule with affinity for a molecule of the invention, such as for SEQ ID NO. 1, SEQ ID NO: 2, SEQ ID NO. 3_-SEQ ID NO. 4. SEQ ID NO. 5, SEQ ID NO. 6 or SEQ ID NO. 7, or such as for one or more of Tyr10 glycosylated SEQ ID 1-7; Abeta 1-X, Tyr10 glycosylated Abeta 1-15, and/or Tyr10 glycosylated Abeta-24-15.

In further embodiments the invention relates to the antibody or antibody-like molecule of the invention selected from the group consisting of monoclonal antibody, polyclonal antibody, Fab fragments, anticalins, affilin, affibodies and single chain antibody.

In further embodiments the invention relates to the peptide according to invention, the composition according to the invention or the antibody or antibody-like molecule of the invention disclosed above for use in medicine, diagnosis or prognosis.

In further embodiments the invention relates to a molecule which binds to an O-linked glycosylation at a Tyrosine residue in a mammalian protein for use in medicine or diagnosis. In further embodiments the invention relates to said use in medicine wherein said molecule is a lectin. The use may for example be wherein said lectin is selected from the group comprising or consisting of ML-1 from mistletoe; Lectin from *Maackia amurensis*; Lectin from *Agrocybe cylindracea*; Lectin from *Agrocybe cylindracea*; and Lectin from *Maackia Amurensis*. In further embodiments the invention relates to said use according to the invention in prevention or treatment of cortical atrophy, neuronal loss, region-specific amyloid deposition, neuritic plaques, and neurofibrillary tangles. In further embodiments the invention relates to the said use according to the invention to treat or prevent a disease where amyloid beta plaque deposition is implicated. In further embodiments the invention relates to the use according to the invention wherein the disease is selected from the group consisting of cerebral amyloid angiopathy and Alzheimer's disease or HIV associated neurocognitive diseases. In further embodiments the invention relates to said use according to the invention for prevention or treatment of Alzheimer's Disease. In further embodiments the invention relates to the further medical use of tunicamycin for treatment or prevention of Alzheimer's disease. In further embodiments the invention relates to the further medical use of streptiviridin for treatment or prevention of AD.

The invention relates in a further aspect to the use of a molecule of the invention, or the antibody or anti-body like molecules of the invention to detect O-linked glycosylation at a tyrosine in a mammalian protein. The term mammalian protein refers to a protein which is present in a mammal. The said protein may also be present in other organisms.

In further embodiments the invention relates to the use of a molecule according to the invention, or the antibody or antibody-like molecule of the invention, to detect O-linked glycosylation at a Tyrosine in a mammalian protein.

In further embodiments the invention relates to the use of a molecule which binds to an O-linked glycosylation at Tyrosine residue to detect O-linked glycosylation at a Tyrosine residue in a mammalian protein. In further embodiments the invention relates to said use according to the invention in a method for diagnosis or prognosis of a disease in a mammal, such as a disease wherein amyloid deposit is implicated, such as a disease selected from the group comprising or consisting of cerebral amyloid angiopathy and Alzheimer's disease, such as diagnosis or prognosis of Alzheimer's disease.

In further embodiments the invention relates to said use of the invention in diagnosis wherein said molecule is an antibody or antibody-like molecule according to the invention or a lectin. In further embodiments the invention relates to an in vitro method for diagnosing or prognosing Alzheimer's disease in a subject, or determining whether a subject is at increased risk of developing Alzheimer's disease, comprising: a. determining the amounts of Abeta peptide with O-linked Tyr10 glycosylation in a sample; and b. comparing said level to a reference value representing a known disease or health status, wherein a varied level in said sample relative to a said reference value representing a known health status indicates a diagnosis, or prognosis, or increased risk of Alzheimer's disease. In further embodiments the method of the invention relates to a method wherein step a) comprises determining the amount of Abeta peptide with O-linked Tyr10 glycosylation relative to unglycosylated Abeta peptide. Further embodiment relates to a method according to claim 1, wherein step a) comprises determining the amount of unglycosylated Abeta peptide relative to the total amount of Abeta peptide for indirect determination of Tyr10 glycosylated Abeta amount.

In further embodiments the invention relates to a method of diagnosis of a disease comprising the steps of a) determining in vitro the amount of Tyr10 glycosylated Abeta peptides; b) determining the amount of unglycosylated Abeta peptides in said sample; comparing the value from a) to the value from b); and c) comparing the relative abundance of Tyr10-glycosylated Abeta peptides to those present in healthy individuals or patients with non-AD dementia. In one embodiment of this method of the invention, Abeta 1-42 is excluded from determination in step b). One embodiment relates to the method according to the invention, wherein step a) comprises determining the amount of Abeta peptide with O-linked Tyr10 glycosylation relative to unglycosylated Abeta peptide.

In a further aspect, the invention relates to compositions for the treating or preventing disease in which amyloid deposit is implicated, such as wherein the disease is selected from the group consisting of cerebral amyloid angiopathy and Alzheimer's disease and HIV associated neurocognitive diseases, such as wherein the disease is Alzheimer's Disease. In one embodiment the invention relates to a composition comprising a mixture of N-acetylhexosamines (N-acetylGalNAc, N-acetylGlcNAc and N-acetylManNAc, 1:1:1 by weight) and at least one suitable excipient. In a further embodiment the invention relates to a composition of the invention for use in medicine. In a further embodiment the invention relates to a composition of the invention in treating or preventing diseases in which amyloid deposit is implicated, such as wherein the disease is selected from the group comprising or consisting of cerebral amyloid angiopathy and Alzheimer's disease and HIV associated neurocognitive diseases, such as wherein the disease is Alzheimer's Disease In one aspect, the invention features a method for diagnosing or prognosing Alzheimer's disease in a subject, or determining whether a subject is at increased risk of developing Alzheimer's disease, comprising: determining the level of O-linked glycosylation at Tyr10 of Abeta in a sample taken from said subject; and comparing said level to a reference value representing a known disease or health status, wherein a varied level in said sample from said subject relative to a said reference value representing a known health status indicates a diagnosis, or prognosis, or increased risk of Alzheimer's disease in said subject.

Thus the invention in one aspect relates to an in vitro method for diagnosing or prognosing Alzheimer's disease in a subject, or determining whether a subject is at increased risk of developing Alzheimer's disease, comprising:
a. determining the level of O-linked glycosylation at Tyr10 of Abeta or APP in a sample; and
b. comparing said level to a reference value representing a known disease or health status, wherein a varied level in said sample relative to a said reference value representing a known health status indicates a diagnosis, or prognosis, or increased risk of Alzheimer's disease. One embodiment relates to the in vitro diagnostic method according to the invention wherein the absolute amount of one or more of Tyr10 glycosylated Abeta peptides is determined. One embodiment relates to the in vitro diagnostic method according to the invention wherein the amount of one or more of Tyr10 glycosylated Abeta peptides is determined relative to one or more non-glycosylated Abeta peptides.

The sample can be a biological sample or fluid such as CSF (cerebrospinal fluid), serum, urine, whole blood, lymphatic fluid, plasma, saliva, cells, tissue, and material secreted by cells or tissues cultured in vitro. Methods for obtaining such a sample are known in the art. If necessary, the sample can be pretreated to remove unwanted materials.

The relative or absolute increase in Tyr10 glycosylated Abeta peptides vs. unglycosylated Abeta peptides in e.g. CSF from AD patients is generally at least 10% in comparison to controls. Preferably, this increase is between 20 and 500%, or for example between 300-1000%. More preferably the increase is between 30 and 500%. The increase may be between 20 and 1000%, such as between 300 and 600%, or for example between 400% and 800%, or for example between 100 and 600%. The increase may be at least 20%, such as at least 50%, at least 100%, at least 200%, at least 350%, at least 400%, or at least 450%. The increase may for example be 50-200% or 100-500%, or 100-300%, or 20-100%. More preferably, the increase in O-linked glycosylation at Tyr10 of the Abeta sequence is 25-100%. Most preferably, the increase in O-linked glycosylation at Tyr10 of the Abeta sequence is 30-70%. Most preferably the increase in O-linked glycosylation at Tyr10 of the Abeta sequence is between 30 to 500%. The concentrations of single glycosylated Abeta peptides in CSF will preferably be in the range of 0, 1-1000 nanogram/L. More preferably, the concentrations of single glycosylated Abeta peptides in CSF will be in the range of 1-100 nanogram/L. The limit of detection will preferably be less than 100 picogram/L, and more preferably less than 10 picogram/L, for each glycopeptide. For assays measuring all glycopeptides carrying a glycan at Tyr10 (Abeta numbering) the range of glycopeptide concentrations in CSF will preferably be 0, 1-5000 nanogram/L, such as between 0.1 and 1500 ng/L, for example between 0.1 and 1000 ng/L, such as between 0.1 and 500 ng/L. More preferably, for assays measuring all glycopeptides carrying a glycan at Tyr10 (Abeta numbering) the range of glycopeptide concentrations in CSF will preferably be 1-1000 nanogram/L, such as between 50 and 100 nanogram/L, for example from 50 to 90 nanogram/L, such as between 75 and 100 nanogram/L. For assays measuring all glycopeptides carrying a glycan at Tyr10, the limit of detection should preferably be in the same range and not higher than any assay measuring the individual components, i.e. less than 10-100 picogram/L, for example less than 100 picogram/L, such as less than 80 picogram/L, such as less than 50 picogram/l, for example less than 20 picogram/L. This is below the detection limit of most conventional ELISA methods but is feasible with single molecule detection (See Example 4c). An enrichment step might however be necessary before performing the analysis. Additionally, although a traditional ELISA using two anti-peptide antibodies will most likely measure the sum effect of all peptides and not the individual peptides with our strategy of combining anti-peptide and anti-carbohydrate antibodies (proteins) we will have a good chance of measuring individual glycopeptides similar to what is possible with the LC-MS analyses published, see further description below.

The level of Tyr10 glycosylation of Abeta in a sample can be quantified using methods familiar to a person skilled in the art. These methods include, but are not limited to, Enzyme-linked immunosorbent assays (ELISAs) including Plasmon-enhanced colorimetric ELISA or other single molecule immunoassays using fluorescent lipid vesicles as enhancer elements, mass spectrometry (MS), positron emission tomography-computed tomography (PET), magnetic resonance imaging (MRIRadioimmunoassays (RIAs), lectin based assays, immunohistochemistry (IHC) methods, western blotting (WB), flow cytometry and similar sorbent-based assays, metabolic, enzymatic or chemical labeling with either isotopic, radioactive, fluorescent or chemically reactive monosaccharides or their precursors, liquid chromatography based methods or direct chemical reactions with either isotopic, radioactive, fluorescent or chemically reactive reagents with constituent monosaccharides or their precursors of the Tyr10 glycan of Abeta. The level of glycosylation of Tyr10 of Abeta can be determined and quantified using a method, or a combination of methods, as mentioned above. Thus the invention relates in one aspect to a method or combination of methods wherein the determination of the level of O-linked glycosylation at Tyr10 of Abeta is performed by a method or combination of methods selected from the group comprising or consisting of the methods listed above.

In preferred embodiments, the subject for diagnosis, according to the present invention, can be a human, an experimental animal, e.g. a mouse or a rat, a fish, a domestic animal, or a non-human primate. The experimental animal can be an animal model for a neurodegenerative disorder, e.g. a transgenic mouse, which express parts of or the whole human sequences of the amyloid precursor protein and/or a knockout mouse, a knock-in mouse or other experimental animal with an AD-type neuropathology.

The invention further pertains to the use of antibodies specific for the Tyr10 of Abeta and antibodies specific for Tyr10 glycosylation of Abeta for determinations of the level of glycosylation at Tyr10 of Abeta, such as the use of an antibody for determination of the level of glycosylation at Tyr10 of Abeta or APP. Suitable methods for assaying this level of glycosylation of Abeta using antibodies specific for the glycosylated Tyr10 of Abeta are immunosorbent or immunoassays such as ELISAs (including Plasmon-enhanced colorimetric ELISA or other single molecule immunoassays using fluorescent lipid vesicles as enhancer elements), RIA, Western blotting or dot blotting, bioimaging methods such as PET-CT and MRI, immunohistochemistry or fluorimetric techniques for whole bodies or organs, cells and tissues or body fluids. The method or methods would be suitable to follow treatment efficacy in clinical trials and suitable for diagnosis of Alzheimer's disease. Thus the invention relates to these methods.

The invention further pertains to the use of antibodies specific for the glycosylated Tyr10 of Abeta in combination with lectins or other carbohydrate binding biomolecules for determination of the level of glycosylation at Tyr10 of Abeta.

Suitable methods for assaying the level and structure of O-glycosylation of Abeta using a combination of antibodies and lectins are immunoassays such as ELISA (including Plasmon-enhanced colorimetric ELISA or other single molecule immunoassays using fluorescent lipid vesicles as enhancer elements), RIA, Western blotting or dot blotting, bioimaging methods such as PET-CT and MRI, immunohistochemistry or fluorimetric techniques for whole bodies or organs, cells and tissues or body fluids. The method would be suitable to follow treatment efficiency in clinical trials and suitable for diagnosis of Alzheimer's disease.

The invention further pertains to the use of antibodies specific for the glycosylated Tyr10 of Abeta for determination of the level of glycosylation at Tyr10 of Abeta in imaging for detection, localization and quantitation. The antibody could be covalently labeled with a detectable label such as a fluorescent ligand such as, but not limited to, fluorescein that have been coupled to available lysine residues on the antibody via the use of a succinimidyl ester of fluorescein. Alternatively, a secondary antibody that is fluorescently labeled can be used for detection of bonded primary antibodies. Alternatively the antibody could be coupled to fluorescently labeled lipid vesicles carrying on the order of 1.000 to 10.000 fluorophores. A radioactive ligand such as $^{131}I$, $^{14}C$, $^{3}H$ or $^{68}Ga$, but not limited to these radioisotopes, for detection purposes may also be used. The method will be suitable for diagnosis of Alzheimer's disease. Alternatively, the antibody could be covalently labeled with a biotin label that has been coupled to available lysine residues on the antibody via the use of a succinimidyl ester of biotin. The amount of bound biotinylated antibody is measured by adding streptavidin linked to a reporter molecule such as horse radish peroxidase or a fluorescent label.

The invention further pertains to the use of metabolic, enzymatic or chemical labeling of APP for detection and quantification of Abeta glycopeptides or Abeta peptides in bioimaging and mass spectrometry based assays. Suitable methods for assaying this level of glycosylation involve, but are not limited to, metabolic, enzymatic or chemical labeling of constituent monosaccharides of the Tyr10 glycan of Abeta or constituent amino acids of Abeta glycopeptides or Abeta peptides, with either isotopic, radioactive or chemically reactive monosaccharides, amino acids, probes or compounds for downstream applications including, but not limited to, bioimaging and mass spectrometry based methods. The method will be suitable to follow treatment efficiency in clinical trials and suitable for diagnosis of Alzheimer's disease.

The invention further pertains to the use of direct chemical reactions for determinations of the level of glycosylation at Tyr10 of Abeta. Suitable methods for assaying this level of glycosylation involve, but are not limited to, chemical reactions with acetyl-, N-acetyl-, N-glycolyl-, hydroxyl-, or carboxyl-functional groups of constituent monosaccharides of the Tyr10 glycans for downstream applications including, but not limited to, enzymatic or chemical labeling with isotopic, radioactive or chemically reactive probes, compounds, antibodies, lectins or other biomolecules in detection assays familiar to a person skilled in the art. The method will be suitable to follow treatment efficiency in clinical trials and suitable for diagnosis of Alzheimer's disease.

The invention further pertains to the use of direct chemical reactions for determinations of the level of glycosylation at Tyr10 of Abeta. Suitable methods for assaying this level of glycosylation involve mild oxidation, preferably by, but not limited to, periodate or periodic acid, of vicinal hydroxyl groups of sialic acids or oxidation, preferably by, but not limited to, periodate or periodic acid, of vicinal hydroxyl groups of hexose and N-actetylhexosamine residues followed by chemical ligation or conjugation with aldehyde reactive probes for signal detection or amplification including, but not limited to, amine-, hydrazide- or oxime-containing probes, chemical compounds, antibodies, lectins or other biomolecules in detection assays such as ELISA, RIA, Western blotting or dot blotting. Mild oxidation may be performed either before or after catching the glycosylated Abeta peptide with the first antibody. The methods will be suitable to follow treatment efficiency in clinical trials and suitable for diagnosis of Alzheimer's disease.

The invention further pertains to the use of direct chemical reactions for determinations of the level of glycosylation at Tyr10 of Abeta in liquid chromatography based assays. Suitable methods for assaying this level of glycosylation involve mild oxidation, preferably by, but not limited to, periodate or periodic acid, of vicinal hydroxyl groups of sialic acids or oxidation, preferably by, but not limited to, periodate or periodic acid, of vicinal hydroxyl groups of hexose and N-actetylhexosamine residues followed by chemical reaction with aldehyde reactive fluorescent, luminescent or other photoactive probes for detection in assays including, but not limited to, reversed phase-, forward phase-, size exclusion or ion exchange chromatography. The method will be suitable to follow treatment efficiency in clinical trials and suitable for diagnosis of Alzheimer's disease.

Antibodies that recognize the Tyr10 glycosylations can be used in different immunosorbent assays to measure concentrations of Abeta Tyr10 glycosylation in samples and to diagnose AD.

The isotypes and affinities of suitable antibodies for the antigen vary extensively from one antibody to the next, and thus the specificity to glycosylated Tyr10 of Abeta is the critical identifying characteristic of these antibodies. The identification of the specificity of an antibody is within the reach of a person skilled in the art.

Examples of preferred antibodies include, but are not limited to, Antibody GD3, Clone: S2-566, Mouse IgM; Antibody ganglioside GD3, Clone: GMR19, Mouse IgM; Antibody Ganglioside O—Ac-GD3, Clone: GMR2, Mouse IgM; Antibody Ganglioside GT1a, Clone: GMR11, Mouse IgM which all are available for purchase from Northstar bioproducts. These antibodies recognize NeuAc-NeuAc which is present on many of the Abeta Tyr10 glycosylations. JONES antibody that recognizes 9-O-acetyl-NeuAc may also be used (Blum and Barnstable (1987) PNAS. 84: 8716-8720). Several monoclonal antibodies raised against polysialic antigens of *E. coli* K1 and *Neisseria meningitidis* type B capsid polysaccharides cross react with polysialic acids found on N-CAM and are likely to react with a polysialic acid structure of the glycan linked to Tyr10 (Abeta numbering) (Sato et al JBC 1995, 270, 18923-28).

Thus one embodiment of the invention relates to the method which is an immunosorbent assay such as an ELISA. A further embodiment of the invention relates to the method wherein the immunosorbent assay such as an ELISA comprises the steps of a. contacting a sample with a capture ligand under conditions that allow the target molecule to bind to the capture ligand; b. subsequently contacting the capture ligand: target molecule complex with a detection ligand; c. detecting the detection ligand using a detectable label conjugated to a binding moiety with affinity for the detection ligand, and d. determining the level of the level of O-linked glycosylation at Tyr10 of Abeta by quantifying the detectable label. See also the Examples. The target molecule is in one embodiment an Abeta peptide carrying a glycosylation on Tyr10. In another embodiment the target molecule is APP carrying a glycosylation on Tyr10. The term "capture ligand" refers to a binding moiety with affinity for the target molecule. In one embodiment, the capture ligand is immobilized on a support, such as for example a microtiter plate or beads. The term "detection ligand" refers to a binding moiety with affinity for the target molecule. In one embodiment the detection ligand binding site is different from the capture ligand binding site. The detection ligand may in one embodiment be detected by a binding moiety having affinity for the detection ligand and being conjugated to a detectable label. Examples of detectable labels are given above. In another embodiment the detection ligand may be dispensed with, as the detectable label being directly conjugated to the target molecule. See above for discussion of direct metabolic, enzymatic or chemical labeling of APP and/or Abeta for detection and quantification of Abeta glycopeptides and Abeta peptides.

In one embodiment the invention relates to an immunosorbent or ELISA or other immunoassay method wherein the capture ligand has affinity for the Abeta peptide and the detection ligand has affinity for the O-linked glycosylation at Tyr10. An alternative embodiment relates to an immunosorbent or ELISA or other immunoassay method wherein the capture ligand has affinity for the O-linked glycosylation at Tyr10 peptide and the detection ligand has affinity for the Abeta peptide. A further embodiment relates to an immunosorbent or ELISA or other immunoassay method wherein at least one of the capture ligand and the detection ligand has affinity for the combination of O-glycosylation at Tyr10 on Abeta and Abeta peptide backbone.

The invention further relates to the use of an antibody or antibody-like molecule of the invention with affinity for the combination of O-glycosylation at Tyr10 on Abeta and a part of the Abeta peptide backbone in a method of diagnosis. In further embodiments the invention relates to said use in methods of diagnosis for a disease in which amyloid deposit is implicated, such as cerebral amyloid angiopathy or AD or HAND, such as AD. The invention further relates to a diagnostic method such as an ELISA wherein the capture ligand or the detection ligand is an antibody or antibody-like molecule with affinity for the combination of O-glycosylation at Tyr10 on Abeta and a part of the Abeta peptide backbone.

The invention further relates to a diagnostic method such as an immunosorbent method, such as ELISA wherein the capture ligand or the detection ligand is an antibody or antibody-like molecule with affinity for the glycosylation at Tyr10 on Abeta glycopeptide 1-x and/or Tyr10 on APP.

The invention further relates to an immunosorbent method, such as an ELISA method of the invention wherein the detectable label is conjugated to the detection ligand. Examples of such direct labeling are given above. The invention further relates to an immunosorbent or ELISA method of the invention wherein the detectable label is conjugated to a moiety having affinity for the detection ligand. Examples of such detectable label conjugated to a moiety having affinity for the detection ligand include for example antibody conjugated to for example a fluorescent ligand, as disclosed above.

In one embodiment the invention relates to an immunosorbent or ELISA method wherein the capture ligand of step a) is selected from the group consisting of anti-amyloid beta antibody. In one embodiment the invention relates to an immunosorbent or ELISA method wherein the detection ligand of step b) is selected from the group comprising or consisting of for example metabolic, enzymatic or chemical labeling, such as peroxidase conjugate. In one embodiment the invention relates to an immunosorbent or ELISA method wherein the capture ligand is the anti-human amyloid beta (N) 82E1 mouse IgG monoclonal antibody; the detection ligand is biotinylated Antibody GD3, Clone: S2-566, Mouse IgM; the detectable label conjugated to a binding moiety with affinity for the detection ligand is peroxidase conjugated to Streptavidin; and the quantifying of the detectable label is done by optically reading the signal output generated by a peroxidase-TMB reaction at 450 nm. See also Examples.

In another embodiment the immunosorbent or ELISA method of the invention comprises the steps of a. conjugating the target molecule to a binding ligand; b. contacting a sample with a capture ligand under conditions that allow the target molecule to bind to the capture ligand; c. detecting the target molecule using a detectable label conjugated to a moiety with affinity for the binding ligand, and d. determining the level of the level of O-linked glycosylation at Tyr10 of Abeta by quantifying the detectable label. A further embodiment relates to the immunosorbent or ELISA method of the invention wherein the capture ligand is the anti-human amyloid beta (N) 82E1 mouse IgG monoclonal antibody; the binding ligand is biotin; the detectable label conjugated to a moiety with affinity for the binding ligand is peroxidase conjugated to streptavidin; and the quantifying of the detectable label is done by optically reading the signal output generated by a peroxidase-TMB reaction at 450 nm.

Further embodiments of the invention relate to the method wherein the capture ligand has affinity for the combination of O-glycosylation at Tyr10 on Abeta and Abeta peptide backbone.

In one embodiment the immunosorbent or ELISA method of the invention relates to a method wherein the method is Plasmon-enhanced colorimetric ELISA or optical single molecule immunoassays using fluorescent lipid vesicles as detectable labels.

The invention further relates to a kit of parts for performing the method of the invention disclosed. A further embodiment relates to said kit wherein said kit comprises a capture ligand having affinity for the Abeta peptide and/or a detection ligand having affinity for the O-linked glycosylation at Tyr10. See also Examples.

In one embodiment the invention relates to an alternative way of assaying the glycosylated vs non-glycosylated APP/Abeta peptides comprising to assay for the various APP/Abeta peptides (irrespective of Tyr substitution) and then assay for all APP/Abeta peptides with a free (non substituted) tyrosine10. Such an assay will need an antibody specific for free Tyr of the APP/Abeta sequence which is also included in this invention. Such a subtraction of free Tyr10 peptides will not take into account any other substitutions of Tyr10 such as nitration, phosphorylation, sulfation or any other derivatization compatible with a tyrosine residue or any of the amino acids surrounding this specific residue and possibly making the epitope cryptic. Such an assay will thus be a less precise estimate than a direct determination of the glycosylated part.

Alternatively, the amount of free (non substituted) tyrosine10 of various APP/Abeta peptides can be estimated by combining e.g. immunoassay based methods, using antibodies specific for any APP/Abeta epitope, with direct chemical reactions for specific or non-specific derivatization of free (non-substituted) tyrosine10 of various APP/Abeta peptides. Free (non-substituted) tyrosine10 can be modified (derivatized) through various chemical reactions due to the ring activating nature of the phenolic group (—C6H6OH) of tyrosine10. These chemical reactions are known to a person skilled in the art. Using oxidants, tyrosine10 can be chlorinated, iodinated, undergo nitrosylation or hydroxylation. Additional chemical modifications of free (non substituted) tyrosine10 include, but are not limited to, electrophilic aromatic substitutions, addition reactions, reactions with succinic anhydride (ester bond formation at phenolic oxygen), tetranitromethane and sodium dithionate (introducing amino groups at ortho position) followed by reaction with sodium nitrate (converting amino group into diazonium derivative), maleylation of the phenolate of tyrosine10, reaction with isothiocyanate compounds, reaction with bis-Diazotized o-Tolidine or p-Diazobenzoyl Biocytin. The principles and chemical compounds used for modification of free (non substituted) tyrosine10 mentioned above can be further modified by a person skilled in the art to introduce any functional group, any detectable label or any enhancer element, e.g. biotin or fluorescent ligand, at this position (tyrosine10 of APP/Abeta peptides). These chemical modifications of free (non substituted) tyrosine10 of various APP/Abeta peptides can then be detected and quantified using a method, or a combination of methods, including, but not limited to, mass spectrometry (MS), positron emission tomography-computed tomography (PET), magnetic resonance imaging (MRI), Enzyme-linked immunosorbent assays (ELISAs) including Plasmon-enhanced colorimetric ELISA or other single molecule immunoassays using fluorescent lipid vesicles as enhancer elements, Radioimmunoassays (RIAs), lectin based assays, immunohistochemistry (IHC) methods, western blotting (WB), flow cytometry or similar sorbent-based assays.

Examples of antibodies for use in methods of the invention are 6E10 antibody (Abeta epitope; F4RHDSG9, Signet Laboratories, Inc., Dedham, Mass., USA)

Anti-human amyloid beta (N) 82E1 antibody (Abeta epitope; N-terminal Abeta, IBL International GmbH, Hamburg, Germany); 8G7 antibody (Abeta epitope; C-terminus of human Abeta1-42, Enzo Life Sciences, Villeurbanne, France); 19B8 antibody (Abeta epitope GY10; Abcam, Cambridge, UK); sAPP alpha (2B3) Antibody (APP epitope; C-terminus of human sAPP alpha, IBL International GmbH, Hamburg, Germany); Anti-Amyloid, β 1-40 (Abeta epitope; A 7 amino acid peptide sequence from the C terminus of human beta-amyloid 1-40, Chemicon/Millipore); Mouse anti Human Amyloid beta A4 protein CV9 7B10 (Abeta epitope; 8 last amino acid residues of Abeta1-40, Acris Antibodies GmbH); Mouse anti Human Amyloid beta 11H3 (Abeta epitope; Free N-terminus of Abeta required, Acris Antibodies GmbH).

Antibodies to the carbohydrate antigen structure at Tyr10 of Abeta, such as an antibody having affinity for the combination of O-glycosylation at Tyr10 on Abeta and Abeta peptide backbone, may be prepared by known methods. These methods include, but are not limited to, monoclonal antibodies based on hybridomas, and polyclonal antibodies or antisera, produced in mice, rabbits, rats, goats, or any other types of animals that are suitable. The methods also include antibody production by the phage display technology and other techniques based on non-immunoglobulin molecules such as affibodies and related techniques. The invention also includes antibody-like molecules having affinity for the combination of O-glycosylation at Tyr10 on Abeta and Abeta peptide backbone. Examples of antibody and antibody-like molecules include antibody, monoclonal antibody, polyclonal antibody, fab fragments, single chain antibody and affibody.

In this context reference to antibodies to the carbohydrate antigen structure at Tyr10 of Abeta includes antibodies which recognize such as an antibody having affinity for the combination of O-glycosylation at Tyr10 on Abeta and Abeta peptide backbone, Natural or synthetic antigens, either single glycopeptide species of or mixtures of the Abeta 1-X series of glycopeptides, either free or linked to or admixed with another (adjuvant) protein and containing the complete structure or partial structure of the following carbohydrate epitopes linked to Tyr10 (Abeta numbering), may preferentially be used to raise such antibodies: NeuAc-Hex-HexNAc-O—; NeuAc-Hex-(NeuAc)-HexNAc-O—; NeuAc-NeuAc-Hex-(NeuAc)-HexNAc-O—; O-AcetylNeuAc-NeuAc-Hex-(NeuAc)-HexNAc-O—; and lactonized NeuAc-NeuAc-Hex-(NeuAc)-HexNAc-O—, where NeuAc is neuraminic acid, also known as sialic acid, where Hex is e.g. a hexose which has galactose, glucose or mannose structure; where HexNAc is N-acetylhexosamine which has e.g. N-acetylgalactosamine, N-acetylglucosamine or N-acetylmannosamine structures. For lactonized NeuAc-NeuAc-Hex-(NeuAc)-HexNAc-O— the two terminal sialic acids have formed an intramolecular lactone (ester bond) and expelled water. For O-AcetylNeuAc a second acetyl group is attached to the sialic acid. Alternative immunogens (antigens) are the glycopeptides Abeta-3-15, 4-15 and 4-17 which contain the oligosaccharides described above linked to Tyr10 (Abeta numbering), which may be used in a similar manner. Alternatively, a crossreacting antibody could be raised towards the mentioned glycan structure where the glycan is linked to e.g. Ser8 of the Abeta sequence.

Examples of such structures include, but are not limited to, Sialyl-Tn and Sialyl-T linked to Ser8 of the Abeta sequence.

A specific issue with anti-carbohydrate antibodies is that carbohydrate antigens often are less immunogenic than peptide/protein antigens and therefore adjuvant mixtures are important for a good immune response. An advantage when using human Abeta peptides and glycopeptides as immunogens is that in mice and rat tyrosine 10 (Abeta numbering) is replaced with phenylalanine which cannot be glycosylated. Thus, Tyr10 glycosylated Abeta peptides are good immunogens for mice and rats, although the use of adjuvants to boost the general or specific immune response should not be precluded.

Furthermore, the glycan structure we have identified on tyrosine 10 may be identical to the terminal glycan epitopes that are described for gangliosides. This includes but is not limited to GD3, GQ1b, GQ1b-alpha, GT1a, GT1a-alpha, GM1b, GD1c and GD1-alpha (Essentials of Glycobiology, $2^{nd}$ edition 2009, page 132). The 2,8-sialylgalactoside terminals are typical for gangliosides of neuronal tissues but are also found in polysialic acid structures of NCAM (promoting neurite outgrowth and sprouting) and in the capsule polysaccharides of some bacteria (e.g. *E. coli* K1 and *Neisseria meningitidis* type B)).

As an alternative to antibodies recognizing Abeta Tyr10 glycosylation various lectins that bind to sialic acid containing carbohydrate structures may be used to assay Tyr10 glycosylation. These lectins include, but are not limited to, Lectin ML-1 from mistletoe; Lectin from *Maackia amurensis*; Lectin from *Agrocybe cylindracea*; Lectin from *Agrocybe cylindracea*; and Lectin from *Maackia Amurensis*.

In addition, antibodies that recognize Tyr10-glycosylated Abeta, produced by immunizing mice, rabbits or other species with Abeta peptides glycosylated at Tyr10, will be used in combination with antibodies against other parts of Abeta for detection purposes described in this patent. These include, but are not limited to, anti-human amyloid beta 6E10 antibody that recognizes amino acid residues 4-9 of the Abeta sequence; and anti-human amyloid beta 82E1 antibody that recognize a free amino terminal of the Abeta sequence e.g. Asp1 and followed by residues 1-5.

Thus the invention in one aspect relates to the use of an antibody for determination of the level of glycosylation at Tyr10 on Abeta, such as anti-human amyloid beta antibodies. In one embodiment the invention relates to use of an antibody comprising or consisting of anti-human amyloid beta 6E10 and/or anti-human amyloid beta 82E1 antibody, A large (~1 kDa) and negatively charged glycan on Tyr10 (Abeta numbering) will substantially influence the mode upon which this region of APP can interact with the membrane. We state that the conformational (or structural) change of APP induced by the presence of a Tyr10 O-glycosylation (Abeta numbering) will affect gamma-secretase cleavage of APP at positions 40-42 (Abeta numbering), so that it is switched such that the residues at positions 17-20 become the preferred cleavage sites. Secondly, we also state that the conformational (or structural) change of APP induced by the presence of a Tyr10 O-glycosylation (Abeta numbering) will affect cleavage of APP by the enzyme (or enzymes) called alpha-secretase (or secretases), so that it changes the preference for cleavage at positions 15-20 (Abeta numbering). Thirdly, we state that the presence of a Tyr10 O-glycosylation (Abeta numbering) will affect cleavage of APP by the enzyme (or enzymes) called beta-secretase (or beta-secretases, including BACE1, BACE2 and cathepsin B), so that it changes the preference for cleavage at positions 1 and/or 4 and/or 10 and/or 19 and/or 34 (Abeta numbering) in the Abeta sequence. Also, the positioning of a glycan at Tyr10 will be able to block other proteases from cleaving the Abeta sequence, and will modulate which proteolytic endproducts that will finally appear.

Glycosylation of APP at Tyr10 will influence the beta-secretase (BACE1) induced cleavage at Asp1 to produce Alzheimer-associated aggregation-prone Abeta1-42 and other long Abeta peptides. Modulation of this APP/Abeta glycosylation therefore also represents a therapeutic target.

We state that glycosylation of APP at Tyr10 (Abeta numbering) will influence the (BACE1) induced cleavage between amino acids 10-11 in the Abeta sequence as well as BACE2 mediated cleavages of APP, APP/Abeta and Abeta isoforms. Further glycosylation of APP at Tyr10 (Abeta numbering) will also influence cleavages of APP, APP/Abeta and Abeta isoforms by the A disintegrin and metalloprotease (ADAM) family, including, but not limited to, ADAM-9, ADAM-10 and ADAM-17 and other enzymes/proteases, including, but not limited to: insulin-degrading enzyme, neprilysin, endothelin-converting enzyme, plasmin, matrix metalloproteases (MMP), including, but not limited to, MMP-2, MMP-3, MMP-9, angiotensin-converting enzyme, cathepsin B and cathepsin D.

We state that glycosylation of APP at Tyr10 (Abeta numbering) is beneficial since modification of the hydroxyl group of the Tyr10 (Abeta numbering) residue alters the reactive properties of this amino acid. Non-glycosylated Abeta peptides, i.e. with a free hydroxyl group on Tyr10, are known to participate in the production of toxic $H_2O_2$ by a mechanism involving electron donation from the non-glycosylated Tyr10 residue (Pramanik, *J. Am. Chem. Soc.*, In press, DOI: 10.1021/ja204628b). The presence of a glycan on Tyr10 will inhibit the electron donating capacity of Tyr10. Secondly, non-glycosylated Abeta peptides, i.e. with a free hydroxyl group on Tyr10 (Abeta numbering), are more prone to react with nitric oxide (NO). Tyr10 (Abeta numbering) nitration by NO was recently shown to accelerate the aggregation of Abeta peptides and enhance the formation of amyloid plaques (Kummer, *Neuron,* 2011 Sep. 8:71, pp 833-44). The presence of a glycan on Tyr10 will inhibit the nitration of Abeta peptides. Modulation of APP/Abeta glycosylation on Tyr10 therefore also represents a therapeutic target. The possibility that glycosylation of Tyr10 positively affects the innate immune response should be considered as a novel therapeutic strategy. Glycosyltransferases themselves, in particular the acceptor binding domain of a glycosyltransferase, are also useful as binding moieties in the diagnostic assays of the invention. In the absence of a particular glycosyltransferase, for example, the concentration of acceptor moieties tends to increase. As an example, a deficiency of tyrosine glycosylation may cause a dramatic change in non-glycosylated peptides of APP in CSF or cell medium. Thus, one can use the peptide pattern as a detection moiety to determine whether tyrosine glycosylation is deficient in the neuronal cells. Providing glycosylation of Tyr10 suppresses glycosylation of Ser8 of Abeta peptides by any known GalNAc-transferase, measuring the activity of such a GalNAc transferase glycosylating Ser 8 of Abeta can be used to estimate the amount of glycosylated versus non-glycosylated Abeta peptides in a mixture or a biological fluid.

In typical embodiments, the detection moieties are labeled with a detectable label. The detectable labels can be primary labels (where the label comprises an element that is detected directly or that produces a directly detectable element) or secondary labels (where the detected label binds to a primary label, as is common in immunological labeling). A variant of this principle for labeling and detection is the binding of the antibodies to vesicles carrying thousands of fluorophores as an efficient enhancer element. An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred in vitro and in vivo labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags] for protein tagging or for incorporation of fluorophores in lipid vesicles; 5) radioactivity. Other methods for labeling and detection will be readily apparent to one skilled in the art.

Preferred enzymes that can be conjugated to detection reagents or detection ligands of the invention include, e.g., luciferase, and horseradish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl)spiro[1,2-d]oxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art.

In general, a detector that monitors a particular label is used to detect the label. Typical detectors include spectrophotometers, phototubes and photodiodes, microscopes including fluorescence microscopes specifically TIRFM (total internal reflection fluorescence microscopy), scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Commercially available detection moieties such as a detectable label conjugated to a binding moiety with affinity for the detection ligand that are suitable for use in the methods of the invention include SNA-fluorescein isothiocyanate (FITC) lectin (FL-1301, Vector Laboratories, Burlingame Calif.) and biotinylated SNA lectin (B-1305, Vector Laboratories) for alpha 2,3 sialyl galactosides. For detection of alpha 2,6 sialylgalactosides, MAL II-FITC lectin and biotinylated MAL II lectin (B-1265, Vector Laboratories) are examples of suitable detection moieties.

Glycosylation is (in contrast to glycation) related to a specific enzyme linked process catalyzed by specific glycosyltransferases. Although the enzyme/s that catalyzes the first or subsequent steps of the glycosylation of Tyr10 has not yet been defined or identified it is scientifically motivated/sound to assume that this is a unique glycosyltransferase coded for by a unique gene and is uniquely expressed in specific tissues and subcellular compartments, and has a catalytic mechanism or principle similar to or identical to other hitherto identified and characterized glycosyltransferases. This gene may be found not only in humans but also in other living organisms (extending to very primitive organisms and including bacteria (Zarschler et al., (2010) Glycobiology 20(6):787-98)).

An alternative to the not yet identified unique glycosyltransferase glycosylating tyrosine residues is a glycosyltransferase showing relevant cross reactivity, i.e. glycosylating Tyr10 of APP (Abeta numbering) or other mammalian proteins, that may have been already identified although the present specificity (glycosylating tyrosine residues) has remained unknown, unrecognized, considered irrelevant to any biological situation—or not made public. A certain degree of promiscuity (capacity to form not only one but two or more different glycosidic bonds) has been described for several glycosyltransferases (compare hFUT 2,3,4) and relates to not only the glycosyltransferase itself but to the complete catalytic situation determined by pH, redoxpotentials, available (often divalent metal) ions, as well as concentrations of competing enzymes, available substrates (nucleotide or dolichol-Phosphate activated mono- or oligosaccharides) and glycosylation acceptors.

Since the enzyme or enzymes involved in the glycosylation of tyrosine (in this invention defined by the glycans identified in Abeta but also any other structural variant of a glycan having the common nominator of a tyrosine glycosylation) are yet to be identified, this invention relates to any transferase or enzyme that contributes to its biosynthesis and processing. The subcellular site of biosynthesis of tyrosine glycosylated proteins (excluding glycogenin), the transport mechanisms within and through the cells as well as the processing outside of the cell and later incorporation into the cell may vary between different tyrosine glycosylated proteins and cells and thus all these steps may be considered unique for this type of glycosylated proteins.

In the following paragraphs we describe the mechanisms that are inherent to any agent or pathway that may interfere with tyrosine glycosylated proteins at the level of synthesis, transportation, metabolism or interactions with other biological structures or synthetic compounds.

The present invention provides compositions and methods for inhibiting progression of or even regression of AD through pathogenic mechanisms that are in any way mediated by the O-glycosylation of APP particularly O-glycosylation at Tyr10 (Abeta numbering). The invention further pertains to preventive measures such as the modulation of O-glycosylation at Tyr10 before a subject has been diagnosed with AD. Not only the first step of glycosylation of Tyr10 (Abeta numbering) by a HexNAc residue but all steps of elongation and formation of a final di-, tri or polysialylated glycan attached to tyrosine 10 are included in the embodiment. Sialylated glycans may be ligands for cell surface molecules involved in intercellular adhesion and signal transduction, such as, for example, CD22, but may also affect interactions with membrane bound carbohydrates of glycolipids or other glycoproteins and may in this embodiment significantly affect the processing of APP through proteolytic cleavage by a number of enzymes such as but not limited to; alpha-, beta- and gamma-secretases. Since the processing of APP to peptides, e.g. to Abeta-1-42 is considered one of the first steps in the pathogenetic mechanisms of forming amyloid plaques typical for AD brain this invention is directed towards prevention, partial or complete inhibition of this process.

Thus, the invention provides methods of modulating AD in a mammal (preferentially humans or a model of AD in another mammal) by administering to the mammal a therapeutically effective amount of an agent that causes an alteration in the amounts of, the structure of or the position of a (sialylated) glycan present on tyrosine 10 in APP (Abeta numbering) or on the corresponding tyrosine residue of any glycopeptide cleaved from this protein. Methods are also provided for preparing the AD modulating agents as well as various screening assays to identify suitable modulating agents. In addition, the present invention provides screening assays for identifying agents that interfere with synthesis of the glycan of tyrosine 10 of APP (Abeta numbering). Therapeutic and other uses for these compounds are also provided.

In some embodiments, the invention provides methods and compositions for inhibiting AD mediated by direct cleavage of APP. Such methods can involve interfering with the biosynthesis of any step towards the complete glycan structure on Tyr10 (Abeta numbering). Such agents may typically involve either the (nucleotide- or dolichol-phosphate) activation of constituent mono- or oligo-saccharides, their transport to the relevant organelle or the induction or inhibition of expression or activity of critical biosynthetic enzymes (e.g. transporters and glycosyltransferases) involved in this glycan biosynthesis. Alternatively, one can administer an agent (e.g., a glycosidase=glycoside hydrolase) or an agent that affects the expression of a glycosidase, which enzymatically may cleave off parts of or the complete glycan of Tyr10 (Abeta numbering).

In other embodiments, the invention provides methods of inhibiting AD by altering the interaction of Tyr10 glycosylated APP (Abeta numbering) with any other component of the plasma membrane e.g. the interaction of non-glycosylated tyrosine with glycolipids of the plasma membrane. (Fantini and Yahi, Exp rev Mol Med 2010, 12:1-22).

In other embodiments, the invention provides methods of inhibiting AD by administering Abeta peptides with a Tyr10 glycosylation that will interfere with the amyloidogeneic process where Abeta 1-42 and other long Abeta peptides form plaques. In addition, Abeta peptides or Abeta like peptides may be administered where a tyrosine residue will become involved in the tyrosine glycosylation machinery and inhibit or reverse the amyloid plaque process.

Inhibitors of Glycosyltransferases

In one embodiment, the methods involve reducing AD progression by altering the enzymatic activities of glycosyltransferases that are involved in the biosynthesis of the glycans of Tyr10 in APP (Abeta numbering). The biology and biochemistry of enzymes involved in the biosynthesis of specific glycosides of proteins and lipids have been extensively studied. For a review, see, e.g., Datta and Paulson (1997) Indian J. Biochem. Biophys. 34: 157-65; Guo and Wang. (1997) Appl. Biochem. Biotechnol. 68: 1-20; Tsuji (1996) J. Biochem. (Tokyo) 120:1-13.

Glycosyltransferases, the general group of enzymes that catalyze the synthesis of these glycoconjugates, catalyze the transfer of a monosaccharide from a glycosylnucleotide, the donor substrate, to an acceptor substrate. The acceptor substrate may be another glycosyl residue, a polypeptide, or a lipid, depending on the specificity of the transferase. See, e.g., Essentials of Glycobiology, Eds. Varki A, et al, 2nd Ed, 2009, CSH Laboratory Press, New York. Glycosyltransferases are grouped into families based on the type of sugar residue transferred. For example, enzymes that transfer sialic acid are called "sialyltransferases", those that transfer fucose are called "fucosyltransferases," those that transfer hexoses are termed "hexosyltransferases" e.g. galactosyltransferases, those that transfer an N-acetylhexosamine (HexNAc) are called N-acetylhexosaminyltransferases and those that transfer an oligosaccharide are called oligosaccharyltransferases. Sialyltransferases are a family of glycosyltransferase enzymes that add sialic acid residues during oligosaccharide diversification (for review, see, e.g., Harduin-Lepers et al. (1995) Glycobiology 5: 741-758). Glycosylation often starts already in ER (e.g. attachment site N-glycosylation on Asn or first step O-glycosylation (Fuc, Man, Glc on Ser/Thr of proteins) but generally terminates by elongation, fucosylation and sialylation in the Golgi apparatus. Mucin type O-glycosylation is typically initialized by the addition of a GalNAc residue to Ser/Thr in the Golgi compartment. Additionally nuclear or regulatory proteins may be O-GlcNAcylated in the cytoplasm. In many families of glycosyltransferases there are typically 10-15 different enzymes required to elaborate the diverse carbohydrate structures found on glycoproteins and glycolipids of animal cells (see e.g. the glycosyltransferases entry in the CAZy database). Each enzyme makes a defined structure based on the donor and acceptor substrates they utilize, and the anomeric linkage formed in the transfer reaction.

Preferably, the inhibitor is specific for the particular glycosyltransferase of interest, and the glycosyltransferase is one that is not required for synthesis of other oligosaccharides that are not involved in AD pathogenesis. In preferred embodiments, the target glycosyltransferase is an N-acetylhexosaminyltransferase, which catalyzes the addition of the first N-acetylhexosamine to a tyrosine residue in a polypeptide chain preferentially tyrosine 10 of APP (Abeta numbering). In other embodiments the target glycosyltransferase is one of the other glycosyltransferases extending or sialylating the glycan chain of Tyr10 of APP (Abeta numbering). Yet another target transferase is the one that transfers a more complex oligosaccharide to this tyrosine residue. In a final embodiment the target glycosyltransferase is a transferase that is not the biological target for the glycosylation process but which is stimulated to glycosylate tyrosine 10 with an atypic (non human brain) structure. Having identified the target enzyme to be inhibited (e.g., a N-acetylhexosaminyltransferase), many approaches can be used to block its activity. Examples of agents capable of inhibiting enzyme activity include immunoglobulins, suicide substrates, alkylating agents, and various substrate analogs. For a review, see Fersht, Enzyme Structure and Mechanism (2d ed. 1985). The methods of modulating AD pathogenesis by inhibiting glycosyltransferase activity can involve administering to a mammal a compound that is an analog of a substrate donor or acceptor for the glycosyltransferase.

In some embodiments, the inhibitor is a sugar nucleotide or an analog of a donor substrate, e.g., an analog of N-acetylhexosamine or UDP-N-acetylhexosamine. As discussed above, the donor substrates of glycosyltransferases are sugar nucleotides, usually diphosphonucleotides. For example, uridine diphosphosugars are donor substrates for the formation of glycosides of glucose, galactose, N-acetylglucosamine, N-acetylgalactosamine, xylose, and glucuronic acid. Guanosine diphosphosugars are donor substrates for the synthesis of glycosides of mannose and fucose. The glycosides of the sialic acids are formed by transfer from cytidine monophosphosialic acid. Dolichol monophosphate conjugates may also serve as glycosyl donors for glucose, mannose and oligosaccharides ($Glc_3$-$Man_9$-$GlcNAc_2$).

Using this knowledge, one of ordinary skill in the art can readily synthesize a number of sugar nucleotides, which can be tested to identify those capable of maximum inhibition of a specific enzyme. The term "sugar nucleotide" as used herein refers both to sugar nucleotides discussed above and to various analogs thereof that might be synthesized or isolated from natural sources. The number of variations on this structure is limitless. For instance, both the ester linkage between the sugar and phosphate and the anhydride linkage of the pyrophosphate are potential targets of enzymatic cleavage. Replacement of the O—P or C—O linkage with a more stable C—P bond provides nucleotide monophosphate or diphosphate sugar analogs that are more resistant to enzymatic degradation. Such compounds have the potential to selectively inhibit glycoprotein or glycolipid synthesis by acting as substrate analogs of a particular glycosyltransferase. See, e.g., Vaghefi, et al., J. Med. Chem. 30:1383-1391 (1987), and Vaghefi et al., J. Med. Chem. 30:1391-1399 (1987). Glycosyltransferase inhibitors are also described, for example, in U.S. Pat. No. 5,461,143.

Another approach is to replace the monophosphate or diphosphate bridge between the sugar residue and the nucleoside moiety. For instance, the diphosphate bridge can be replaced with an isosteric —$OCONHSO_2O$— residue. See e.g. Camarasa, et al., J. Med. Chem. 28:40-46 (1985).

Analogs of sugar nucleotides capable of inhibiting glycosylation have been used as antibiotics and antiviral agents. Examples of such compounds include 2-deoxy-D-glucose, which is transformed to either UDP-2dGlc or GDP-2dGlc and in that form inhibits glycosylation of glycoproteins in the viral envelope. DeClercq, Biochem. J. 205:1 (1982), which is incorporated herein by reference. Antibiotics such as tunicamycin and streptovirudin are also effective because of their ability to inhibit glycosylation. For instance, tunicamycin is an analog of UDP-GlcNAc, the donor substrate for N-acetylglucosaminyltransferases. The replacement of a diphosphate bridge with a carbon chain allows tunicamycin to cross the cell membrane but still readily bind the active site of the enzyme. The structure of these and related compounds provide one of skill in the art with direction in designing and synthesizing compounds with similar inhibitory effects in accordance with the present invention as described herein. Additional analogs of sialic acid sugar nucleotides that are useful in the methods of the invention include, for example CMP-quinic acid and derivatives thereof. (Schaub et al. (1998) Glycoconjugate J. 15: 345-354). Thus, the invention in one embodiment relates to the use of tunicamycin and/or streptivirudin for the preventing or treating of AD.

Nucleotides are the byproduct of the reaction by which glycosyl residues are transferred to acceptor substrates. Nucleotides have been found to competitively inhibit glycosyltransferase. Thus, various nucleotides and their analogs have potential as inhibitors of these enzymes. For example, CDP and CMP can be used to inhibit sialyltransferase activity. In addition to the donor substrate analogs, analogs of acceptor substrates may also be used as inhibitors. Again, the skilled artisan will recognize a variety of possible structures that can be used. Since the acceptor substrate in the first round of glycosylation of tyrosine is a protein any similar polypeptide or derivative thereof, which specifically interacts with the relevant glycosyltransferase, gives many possibilities for designing an inhibitor. Ideally, the inhibitory compounds should be capable of acting as specific acceptor substrates for a given enzyme, even in the presence of other enzymes. In addition, the compound should be an efficient acceptor substrate. Thus, the $K_i$ of the inhibitor should generally be lower than about $10^{-5}$ M, preferably lower than about $10^{-7}$ and more preferably lower than about $10^{-9}$ M.

Glycosyltransferases can also be inhibited by presenting acceptor substrates for the glycosyltransferase with a competing glycosyltransferase or glycosidase that converts the acceptor oligosaccharide into a different structure that does not function as an acceptor for the glycosyltransferase of interest. For example, one can inhibit ST6Gal sialyltransferase activity on a Gal beta 1,4GlcNAc-containing oligosaccharide by presenting an alpha 1,2 fucosyltransferase (e.g., FucT I or FucT II), which make the oligosaccharide structure Fuc alpha 1,2Gal beta 1,4GlcNAc, or an alpha 1,3 fucosyltransferase (e.g., FucT III, FucT IV) which synthesize the structure Gal beta 1,4(Fuc alpha 1,3)GlcNAc (Paulson et al. (1978) J. Biol. Chem. 253: 5617-5624). Neither of these fucosylated compounds are acceptors for an ST6Gal sialyltransferase. Transformed to the situation of this embodiment the unknown glycosyltransferase glycosylating the tyrosine residue of position 10 in APP (Abeta numbering) could be blocked by a known GalNAc-transferase glycosylating serine residue of position 8 in APP (Abeta numbering). Such a glycosylation is likely to inhibit for sterical reasons. Alternatively, the extension or sialylation of the innermost HexNAc saccharide residue could be inhibited either by a sialyltransferases (e.g. ST6GalNAc-I creating a Sialyl Tn-like antigen) or by a beta1,6-GlcNAc-transferase making the Core 2-like chain and blocking the sialylation of the biological core structure.

Naturally occurring molecules, which show inhibitory effects may also be isolated for use in the present invention. The biosynthesis of glycoproteins (or glycolipids) is a complex metabolic pathway that depends on many factors for regulation. Naturally occurring inhibitory compounds can be purified and used to further inhibit activity. Ammonium chloride and chloroquine also have been reported to inhibit sialyltransferase activity (Thorens et al. (1986) Nature 321: 618).

The preferred glycosyltransferase inhibitors of the present invention have the ability to cross the cell membrane and enter the Golgi apparatus and the endoplasmic reticulum. Thus, the blocking agents are preferably sufficiently hydrophobic to allow diffusion through membranes. Preferably, the blocking agents can pass the blood brain barrier, but if not, they can be modified with carrier molecules known in the art or introduced directly into the CNS, e.g. by intrathecal delivery. Preferably, they have no other adverse effects on cellular metabolism, so that other glycosylation reactions proceed while the specific reaction is inhibited. The blocking agents are preferably relatively small molecules, thereby avoiding immunogenicity and allowing passage through the cell membrane, but relatively large blocking agents are also covered by the invention. Ideally, the relatively small molecules have a molecular weight of between about 100-2000 daltons, but may have molecular weights up to 5000 or more, depending upon the desired application. In most preferred embodiments, the small molecule inhibitors have molecular weights of between about 200-600 daltons.

The inhibitors of the present invention preferably have strong affinity for the target enzyme, preferably more than approximately 70% inhibition of glycosyltransferase activity is achieved, more preferably about 75-85% and most preferably 90-95% or more. The affinity of the enzyme for the inhibitor is preferably sufficiently strong that the dissociation constant, or of the enzyme-inhibitor complex is less than about $10^{-5}$ M, preferably between about $10^{-6}$ and $10^{-8}$ M.

Yet another tactic to inhibit glycosyltransferase activity is to use immunoglobulin molecules raised against the particular enzyme of interest. See, e.g., White et al., Biochem., 29:2740-2747 (1990). Thus, the multitude of techniques available to those skilled in the art for production and manipulation of various immunoglobulin molecules can be applied to inhibit Tyr10 glycosylation. The immunoglobulins may exist in a variety of forms besides antibodies, including for example, Fv, Fab, and F(ab)$_2$, as well as in single chains.

Antibodies, which bind the enzyme may be produced by a variety of means (see above). The production of non-human monoclonal antibodies, e.g., murine, lagomorpha, equine, etc., is well known and may be accomplished by, for example, immunizing the animal with glycosyltransferase or a fragment thereof conjugated to a carrier. Antibody-producing cells obtained from the immunized animals are immortalized and screened, or screened first for the production of antibody, which inhibits the interaction of the enzyme with the substrate and then immortalized. For a discussion of general procedures of monoclonal antibody production, see, Harlow and Lane, Antibodies, A Laboratory Manual (1988).

Enzyme inhibition generally involves the interaction of a substance with an enzyme so as to decrease the rate of the reaction catalyzed by that enzyme. Inhibitors can be classified according to a number of criteria. For example, they may be reversible or irreversible. An irreversible inhibitor dissociates very slowly, if at all, from its target enzyme because it becomes very tightly bound to the enzyme, either covalently or non-covalently. Reversible inhibition, in contrast, involves an enzyme-inhibitor complex, which may dissociate. Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive/allosteric inhibition, in which the inhibitor affects the binding site and also alters the turnover number of the enzyme. Enzyme inhibition of kinetically complex systems involving more than one substrate, as is often the case for glycosyltransferases, is described in Segel, Enzyme Kinetics (Wiley, N.Y. 1975).

Screening Methods for Identifying Blocking Agents

One can identify therapeutically effective blocking agents by screening a variety of compounds and mixtures of compounds for their ability to inhibit glycosyltransferase activity. The use of screening assays to discover naturally occurring compounds with desired activities is well known and has been widely used for many years. For instance, many compounds with antibiotic activity were originally identified using this approach. Examples of such compounds include monolactams and aminoglycoside antibiotics. Compounds which inhibit various enzyme activities have also been found by this technique, for example, mevinolin, lovastatin, and mevacor, which are inhibitors of hydroxymethylglutamyl Coenzyme A reductase, an enzyme involved in cholesterol synthesis. Antibiotics that inhibit glycosyltransferase activities, such as tunicamycin and streptovirudin have also been identified in this manner.

Thus, another important aspect of the present invention is directed to methods for screening samples for glycosyltransferase inhibiting activity. A "sample" as used herein may be any mixture of compounds suitable for testing in a glycosyltransferase assay. The most efficient way is usually to screen libraries of chemical compounds (High Throughput Screening), which may become even more efficient after computer screening of possible candidates from larger chemical libraries usually composed of synthetic compounds. Computer screening needs access to crystallographic data of the active site and may also be used to test minor modifications of compound trying to find a lead molecule; compare the development of neuraminidase inhibitor oseltamivir.

A sample for screening may also comprise a mixture of synthetically produced compounds or alternatively a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like. In the typical screening assay of a biological sample, such as a fungal broth, the sample is added to a standard glycosyltransferase assay. If inhibition of activity as compared to control assays is found, the mixture is usually fractionated to identify components of the sample providing the inhibiting activity. The sample is fractionated using standard methods such as ion exchange chromatography, affinity chromatography, electrophoresis, ultrafiltration, HPLC and the like. See, e.g., Protein Purification, Principles and Practice (Springer-Verlag, 1982). Each isolated fraction is then tested for inhibitory activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure blocking agent as defined herein is an inhibitory compound, which migrates largely as a single band under standard electrophoretic conditions or largely as a single peak when monitored on a chromatographic column. More specifically, compositions of substantially pure blocking agents will comprise less than ten percent miscellaneous compounds.

An assay for glycosyltransferase activity typically contains a buffered solution adjusted to physiological pH, a source of divalent cations, a donor substrate (usually isotopically labeled nucleoside-activated monosaccharide), an acceptor substrate (e.g. protein, lipid, or saccharide), glycosyltransferase (typically recombinantly expressed in soluble form but sometimes as membrane bound enzyme), and the sample or fraction of a sample whose inhibitory activity is to be tested. After a predetermined time, the reaction is stopped and the glycosylated product is isolated and measured according to standard methods (e.g., in a scintillation counter). Glycosyltransferase assays which use a UV-labeled acceptor, and lead to a UV-labeled product that can be readily separated by reverse phase HPLC and quantitated by UV spectroscopy are described in Schaub et al. (1998) Glycoconjugate J. 15: 345-354. For a general discussion of enzyme assays, see, Rossomando, "Measurement of Enzyme Activity" in Guide to Protein Purification, Vol. 182, Methods in Enzymology (Deutscher ed., 1990).

In addition to assaying for an effect on purified glycosyltransferase activity in vitro, one may identify suitable modulators of APP processing using cell cultures expressing human APP. The read out then is typically a chromatographic or electrophoretic separation of peptides and glycopeptides identified and characterized by e.g. MS in the cells or in the cell medium.

Inhibition of Glycosyltransferase Gene Expression

Inhibition of glycosyltransferase gene expression can be achieved through the use of inhibitory nucleic acids. Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. These nucleic acids are sometimes termed "antisense" because they are usually complementary to the sense or coding strand of the gene, although approaches for use of "sense" nucleic acids have also been developed. The term "inhibitory nucleic acids" as used herein, refers to both "sense" and "antisense" nucleic acids.

In one embodiment, the inhibitory nucleic acid can specifically bind to a target nucleic acid that encodes a specific sugar-nucleotide transporter or a glycosyltransferase. Administration of such inhibitory nucleic acids may alter the processing of APP by reducing or inhibiting the glycosylation of APP, specifically on Tyr10 residue (Abeta numbering). Nucleotide sequences of such human genes are known from the sequencing of the human genome projects and are stored in open databases. From these nucleotide sequences, one can derive a suitable inhibitory nucleic acid.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene, C. and Toulme, J. (1990) Biochim. Biophys. Acta, 1049:99-125.

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. For details concerning approaches targeting DNA, see the previously mentioned reference from Helene and Toulme 1990.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression. See, e.g., Wickstrom E. L. et al. (1988) Proc. Nat'l. Acad. Sci. USA 85:1028-1032 and Harel-Bellan et al. (1988) Exp. Med., 168:2309-2318. As described in Helene and Toulme 1990, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation (Helene and Toulme 1990).

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids may be affected by attaching a substituent to the inhibitory nucleic acid, which can be activated to induce cleavage reactions. The substituent can be one that affects either chemical, photochemical or enzymatic cleavage. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

In other embodiments, expression of glycosyltransferase genes is inhibited by administration of an agent that blocks the ability of a transactivating factor to induce gene expression. For example, one can administer an agent that interferes with the transactivating activity of tumor necrosis factor-alpha, interleukin-1, glucocorticoids (e.g., dexamethasone), retinoic acid, and some liver transcription factors (e.g., HNF-1, DBP and LAP). HIV-1, human T cell lymphotropic virus type 1 (HTLV-1), cytomegalovirus (CMV), varicella-zoster virus (VZV) and Herpes simplex virus (HSV-1) induce glycan neo-antigens by induced expression of host glycosyltransferases or by coding for viral transferases (Adachi M et al. (1988) J Exp Med 167, 323-331, Cebulla C M et al. (2000) Transplantation 69, 1202-1209, Hiraiwa N et al. (2003) Blood 101, 3615-3621, Nordén R et al Glycobiology. 2009 19, 776-88). The molecular mechanisms responsible for inducing host glycosyltransferase activities (transcription and translation) may be used for increasing glycosyltransferase activity or for identifying proteins for targeted inhibition of expression.

The targeting of inhibitory nucleic acids to specific cells of the nervous system by conjugation with targeting moieties (antibodies, virus-like-particles or other vehicles) binding receptors on the surface of these cells can be used for all of the above forms of inhibitory nucleic acid therapy.

Activation of Glycosylation

In another setting it may be beneficial to increase glycosylation of APP to inhibit or slow down the AD progression or even to regress the disease. As stated above it is likely that a charged glycan linked to Tyr 10 (Abeta numbering) of the APP molecule will change the proteolytic processing of APP. It is important to recognize that glycosylation may not be an all or nothing process but rather a modulating step in APP processing. There are some natural strategies for obtaining an increased glycosylation of APP 1. The balance between de novo protein synthesis of APP, APP folding and glycosylation. In a situation where the de novo APP production is altered (increased) so that the capacity for post-translational modification, such as glycosylation, becomes insufficient the de novo synthesis should be slowed down which can be done by decreased transcription (regulated by transcription factors) of the APP gene, or decreased translation of mRNA to the protein APP, or by increased retention time of APP in the ER (chaperone, N-oligosaccharyltransferase or alpha-glycosidase activity is slowed down).
2. Increased capacity for glycosylation of APP. This effect can be obtained through increased amounts (concentrations at any particular time) of activated donor saccharides in ER, of the glycosyltransferase catalyzing the committed step in ER and in Golgi or by adjustments of pH and concentrations of divalent ions necessary for the enzymatic process to function optimally. An increase in activated donor saccharides could be obtained by oral (or parenteral) administration of the relevant monosaccharides (or their metabolic precursors) as has been successfully tested with orally given mannose for patients with CDGS type 1b to compensate for their phosphomannose isomeras (PMI) deficiency. Although not curative for the disease this oral administration of mannose is well tolerated. A similar situation was the rationale when successfully testing oral administration of fucose to a child with leukocyte adhesion deficiency type II (LAD II). Since many monosaccharides are metabolically interconvertible and we are not dealing with all or nothing effects but rather relative increases in concentrations there are no known toxic or immunogenic complications when administering any of these monosaccharides. Nucleotide transporter for both UDP-GlcNAc and UDP-GalNAc are found both in ER and in Golgi systems and their expression could also be increased—in a similar manner to glycosyltransferases—to increase the first steps of glycosylation of Tyr 10 (Abeta numbering) of APP. An increased expression of either transporters or transferases may well be obtained by an increased transcription of the genes or an increased translation of mRNA, folding and maturation of the relevant enzymes. An increase of transcription may be stimulated by steroid hormones e.g. cortisol, estrogen etc. Finally a suboptimal pH, redoxpotential or concentration of other ions (i.e. mono- or divalent cations) involved in the transport of activated monosaccharides or directly involved in the O-glycosylation of the Tyr 10 residue (Abeta numbering) of APP may be corrected for and optimized by chemical agents or by other homeostatic enzyme activities in the ER and Golgi systems.
3. The possibility of inhibiting inhibitors of glycosylation. Since glycosylation is an enzymatic modification recognizing a specific peptide sequence or a 3D-domain of the protein any alternative modification of neighboring amino acid residues could result in an inhibition of glycosylation. Modifications may be methylations, acetylations, other acylations. Eliminating such derivatizations or derivatives, if they exist, may facilitate glycosylation.

The compositions and methods of the present invention can be used therapeutically to selectively reduce or inhibit one glycosyltransferase or amplify another glycosyltransferase activity associated with a pathogenic processing of APP. In some embodiments, these pathogenic processes are concentrated to some areas of the brain but in others they engage most areas of the brain. The invention can be used to inhibit deleterious or progressive stages of Alzheimer's disease.

In therapeutic applications, the glycosyltransferase inhibitors (or affectors) of the invention are administered to an individual already suffering from an inappropriate or undesirable cognitive defect. Compositions that contain glycosyltransferase inhibitors or agents that bind to and block the glycosyltransferase are typically administered to a patient in an amount sufficient to suppress the undesirable pathological process and to cure or at least partially arrest symptoms and/or complications. An amount adequate to accomplish this is defined as "therapeutically effective dose." Amounts effective for this use will depend on, e.g., the inhibitor composition, the manner of administration, the stage and severity of the disease being treated, the weight and general state of health of the patient, and the judgment of the prescribing physician.

Alternatively, DNA or RNA that inhibits expression of one or more glycosyltransferase inhibitors, such as an antisense nucleic acid or a nucleic acid that encodes a peptide that blocks expression or activity of a glycosyltransferase, can be introduced into patients to achieve inhibition. U.S. Pat. No. 5,580,859 describes the use of injection of naked nucleic acids into cells to obtain expression of the genes, which the nucleic acids encode. Therapeutically effective amounts of the glycosyltransferase affector compositions of the present invention generally range for an initial daily regimen (that is for therapeutic or prophylactic administration) from about 1.0 mg to about 30 g of glycosyltransferase inhibitor/activator for a 70 kg patient, preferably from about 10 mg to about 10 g, and more preferably between about 2 mg and about 1 g. These doses can be followed by repeated administrations over weeks to months depending upon the patient's response and condition by measuring APP derived peptides and glycopeptides in CSF (see assays).

It must be kept in mind that the compositions of the present invention may be employed in serious disease states, that is, life-threatening or potentially life threatening situations. In such cases, in view of the minimization of extraneous substances and the relative nontoxic nature of the inhibitors/activators, it is possible and may be felt desirable by the treating physician to administer substantial excesses of these compositions.

For prophylactic use, administration should be given to risk groups. Therapeutic administration may begin at the first sign of disease or the detection or shortly after diagnosis. This is often followed by repeated administration until at least symptoms are substantially abated and for a period thereafter.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, intrathecally or intramuscularly. Compositions of the invention are also suitable for oral administration. Thus, the invention provides compositions for parenteral administration which comprise a solution of the glycosyltransferase inhibiting/activating agent dissolved or suspended in an acceptable carrier, preferably an aqueous carrier. A variety of aqueous carriers as known in the art may be used, e.g., water, buffered water, 0.9 percent saline, 0.3 percent glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of glycosyltransferase inhibiting/activating agents of the invention in the pharmaceutical formulations can vary widely, i.e. from less than about 0.1 percent, usually at or at least about 2 percent to as much as 20 percent to 50 percent or more by weight, and will be selected primarily by fluid volumes, viscosities, etc., in accordance with the particular mode of administration selected.

The glycosyltransferase inhibitors/activators of the invention may also be administered via liposomes or Virus-like-particles (VLPs) or other nano-vesicles, which serve to target the conjugates to a particular tissue, such as nervous tissue, or to target selectively to cells, as well as increase the half-life of the agent. Liposomes include emulsions, foams, micelles, insoluble monolayers, liquid crystals, phospholipid dispersions, lamellar layers and the like. VLPs are preferentially constructed from Norovirus strains, which show specificity to histo blood group antigens. In these preparations the inhibitor to be delivered is incorporated as part of a liposome, alone or in conjunction with a molecule, which binds to, e.g., a receptor prevalent among neuronal cells, such as monoclonal antibodies, or with other therapeutic or immunogenic compositions. Thus, liposomes filled with a desired agent or conjugate of the invention can be directed to the site of the brain, where the liposomes then deliver the selected glycosyltransferase inhibitor compositions. Liposomes for use in the invention can e.g. be formed from vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods is available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the neuronal cells, a ligand to be incorporated into the liposome can include, e.g., antibodies or fragments thereof specific for cell surface determinants of the desired cells. A liposome suspension containing an agent or conjugate may be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95 percent of active ingredient, that is, one or more conjugates of the invention, and more preferably at a concentration of 25 percent-75 percent.

For aerosol administration, the inhibitors/activators are preferably supplied in a suitable form along with a surfactant and propellant. Typical percentages of glycosyltransferase inhibitors are 0.01 percent-20 percent by weight, preferably 1 percent-10 percent. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1 percent-20 percent by weight of the composition, preferably 0.25-5 percent. A carrier can also be included, as desired, as with, e.g., lecithin for intranasal delivery.

The present invention also provides methods of monitoring APP processing by detecting the levels of APP derived peptides and glycopeptides in a sample from a patient. This can be performed according to standard methods for detection of desired glycopeptides. For instance, specific lectins or antibodies raised against the ligand can be used as has been previously described.

As used herein, a "substantial change" in the appropriate glycosylation levels or glycosyltransferase activity refers to a change of at least about 20 percent in the test sample compared to a non-AD control. Preferably, the change will be at least about 50 percent, more preferably at least about 75 percent, and most preferably glycosylation or glycosyltransferase levels will be changed by at least about 90 percent in a sample from an AD mammal compared to a non-AD control.

In preferred embodiments, the subject for treatment or prevention, according to the present invention, can be a human, an experimental animal, e.g. a mouse or a rat, a domestic animal, or a non-human primate. The experimental animal can be an animal model for a neurodegenerative disorder, e.g. a transgenic mouse and/or a knock-out or knock-in mouse with an AD-type neuropathology In one embodiment the invention relates to a method comprising the steps:
a. Enrichment of Abeta peptides and glycopeptides carrying the O-linked glycosylation on Tyr10 from a sample,
b. Separation of the Abeta peptides and glycopeptides using liquid chromatography,
c. Identification of Abeta peptide and glycan fragments by mass spectrometry and
d. Determination of the level of O-linked glycosylation at Tyr10 of Abeta in relation to Abeta peptides using mass spectrometry.

In one embodiment the invention relates to a method wherein the peaks have been previously identified using mass spectrometry and is performed in Multiple Reaction Monitoring (MRM) mode. In one embodiment the invention relates to a MRM method wherein settings comprise the first quadrupole is set to let through a narrow m/z range of about 1 Da,
in the second quadrupole the ions are subjected to Collision Induced Dissociation (CID),
the third quadrupole lets through a narrow m/z range corresponding to one of the fragment ions produced in CID.
In one embodiment the invention relates to a method wherein four Tyr10-glycosylated Abeta compounds (Neu5AcHex(Neu5Ac)HexNAc-O-(Tyr10)Abeta1-15, Neu5AcNeu5AcHex(Neu5Ac)HexNAc-O-(Tyr10) Abeta1-15, Neu5AcHex(Neu5Ac)HexNAc-O-(Tyr10) Abeta1-17, and O-AcetylNeu5AcNeu5AcHex (Neu5Ac)HexNAc-O-(Tyr10)Abeta1-17) and two unglycosylated Abeta peptides (Abeta1-15 and Abeta1-17) are detected.

In one embodiment the invention relates to a method wherein the enrichment is performed by capture using a capture ligand selected from the group consisting of lectins and immunoglobulins. In one embodiment the invention relates to a method of the invention wherein the capture ligand is an antibody; in a further embodiment the capture is performed by immunoprecipitation. In one embodiment the invention relates to a method wherein the immunoprecipitation employs an antibody selected from the group consisting of an anti-Tyr10 Abeta antibody, an anti-Abeta antibody. In one embodiment the invention relates to a method wherein the antibody is 6E10 (Abeta epitope; $F^4RHDSG9$) (SEQ ID NO:8). In one embodiment the invention relates to a method wherein an ultrahigh pressure liquid chromatography system is used.

EXAMPLES

Example 1

Ethical Consideration and CSF Sampling

This study was performed on CSF samples supplied by the Clinical Neurochemistry Laboratory, Sahlgrenska University Hospital. The study was approved by the local ethical committees and was conducted according to the provisions of the Helsinki declaration. Samples were collected by lumbar puncture from patients who sought medical advice due to cognitive impairment. The samples were primarily designated for use in conventional CSF-based diagnosis, and were subsequently used in this study. For method development, mainly pooled lumbar CSF samples from de-identified healthy individuals were used. These samples came from individuals undergoing lumbar puncture to diagnose for possible brain infection, and were found to be healthy based on normal white cell count and brain blood barrier function. The first 10-12 ml of CSF were collected, centrifuged at 1800 g for 10 min to eliminate insolubles and stored at −80° C. Patients were designated as control or AD according to CSF biomarker levels using cutoffs that together are 90% specific for AD [Hansson, O., Zetterberg, H., Buchhave, P., Londos, E., Blennow, K., Minthon, L.: Association between CSF biomarkers and incipient Alzheimer's disease in patients with mild cognitive impairment: a follow-up study, Lancet neurology 5, 228-234 (2006)]: total tau (t-tau)>350 ng/L, phosphorylated tau (p-tau)>80 ng/L and Abeta42<530 ng/L. None of the control subjects fulfilled all these criteria.

Immunoprecipitation of Abeta.

Immunoprecipitation of APP/Abeta-peptides from CSF was performed according to a previously described protocol [Portelius, E., Tran, A. J., Andreasson, U., Persson, R., Brinkmalm, G., Zetterberg, H., Blennow, K., Westman-Brinkmalm, A.: Characterization of amyloid beta peptides in cerebrospinal fluid by an automated immunoprecipitation procedure followed by mass spectrometry, J Proteome Res 6, 4433-4439 (2007)]. Briefly, the ABeta specific antibody, 6E10 (Abeta epitope; $F^4RHDSG^9$) (SEQ ID NO: 8) (2-10 µg/ml of CSF; Signet Laboratories) was first incubated with sheep anti-mouse IgG conjugated magnetic beads (Invitrogen) over night (+4° C.) followed by a 15 h incubation with 1-10 ml CSF (+4° C.), which had been complemented with 0.025% Tween 20. The beads/CSF solution was transferred to a KingFisher magnetic particle processor (Thermo Scientific) for automatic washing and elution in a 5-step procedure. The beads were washed with 0.025% Tween 20 in PBS, PBS and 50 mM ammonium bicarbonate and ABeta was eluted using 0.5% formic acid (100 ml) at room temperature for 1 min, and evaporated to dryness in a vacuum centrifuge. Prior to liquid chromatography-MS (LC-MS) analysis the samples were redissolved in 5 µl 40% acetonitrile, 40% formic acid, 20% water (v/v/v), vortexed at least 30 min and diluted to 25 ml with water (final composition 8% acetonitrile and 8% formic acid).

Liquid Chromatography/Mass Spectrometry.

Nanoflow liquid chromatography coupled to electrospray ionization Fourier transform ion cyclotron resonance tandem mass spectrometry (LC-ESI-FTICR-MS/MS) was performed with an Ettan MDLC (GE Healthcare) and an LTQ-FT (upgraded to Ultra during the period of data collection; ThermoFisher Scientific). For the liquid chromatography C4 reversed-phase columns were used. A C4 trap column (5 mm×0.3 mm, particle size 5 µm; HotSep Tracy; G&T Septech) was used for online desalting and sample cleanup, followed by a nanoscale C4 column (150×0.075 mm, particle size 5 µm; HotSep Kromasil; G&T Septech). A linear gradient of 0-75% B in A for 50 min at a flow rate of approximately 400 nl/min was used. Mobile phase A was 0.1% formic acid in HPLC grade water, and mobile phase B was 0.1% formic acid in 84% aqueous acetonitrile. The LTQ-FT was operated in data-dependent mode, where a scan cycle consisted of one full scan survey mass spectrum followed by $MS^2$ of the three most abundant ions. The CID ion spectra were acquired in both high resolution FTICR mode and in the high sensitivity mode using the linear ion trap. The collision induced dissociation (CID) collision energy was set to 30. For the ECD acquisitions, the energy was set to 4 and/or 5 with 60-80 ms irradiation time.

Results.

The mass spectrometric data showed that Tyr residues in human proteins can become O-glycosylated with sialic acid-containing glycans. We found that seven Abeta isoforms, such as Abeta1-19 (DAEFRHDSGYEVHHQKLVF) (SEQ ID NO. 9), Abeta1-17 and Abeta1-15 were glycosylated on Tyr10 (Table 2). The glycans were Neu5AcHex(Neu5Ac) HexNAc-O—(Table 1b) and Neu5AcNeu5AcHex(Neu5Ac) HexNAc-O—. We could however not detect any glycosylation of the Abeta1-42, 1-40, 1-39, 1-38, 1-37, 1-34, 1-33, 1-30 or 1-28 isoforms. Abeta 1-20 was the largest Abeta 1-X glycopeptide where it was possible for us to detect Tyr10 glycosylation. While glycan structural information can be obtained from collision induced dissociation (CID) spectra, information about the amino acid position of a glycan can be obtained by electron capture dissociation (ECD). In Table 1a an ECD fragment ion spectrum of Neu5AcHex(Neu5Ac)HexNAc-O-(Tyr10)Abeta1-15 is shown, while Table. 1b shows an ECD fragment ion spectrum of unglycosylated Abeta1-15. The c- and z-ion peptide backbone fragments are annotated and shown in relation to the Abeta sequence. An expansion shows critical peaks in more detail. The crucial peaks are those that distinguish between glycan attachment on Ser8 and Tyr 10, namely singly charged c8 at m/z 975.43, singly charged c9 at m/z 1032.46, and especially doubly charged z6 at m/z 872.35. The latter confirms the existence of the C-terminal ECD ion fragment YEVHHQ (SEQ ID NO. 5) with a mass corresponding to Neu5AcHex(Neu5Ac)HexNAc attached to it. The detected fragments z2-z5 have no glycan attached. The detected c- and z-ions for the ECD fragmentation of Neu5AcHex(Neu5Ac)HexNAc-O-(Tyr10)Abeta1-15 are also presented in table 1a. FIG. 1c is an example of a CID fragment ion spectrum of Neu5AcHex(Neu5Ac)HexNAc-O-(Tyr10)Abeta1-15 showing glycan fragmentation that is used to deduce glycan structure, which is shown in the box. The B- and Y-type fragments (nomenclature according to Domon and Costello, Glycoconj. J 1988), which were generated during CID fragmentation of Neu5AcHex(Neu5Ac)HexNAc-O-(Tyr10)Abeta1-15 are also presented in Table 1b.

TABLE 1a

Mass spectrometric evidence for the glycosylation of Tyr10 of the Neu5AcHex(Neu5Ac)HexNAc-O-(Tyr10)Abeta1-15 glycopeptide. Theoretical and detected c- and z-ions generated by Electron capture dissociation (ECD) are shown.

| Sequence | | Theoretical c-ions | | | Detected c-ions | | | Theoretical z-ions | | | Detected z-ions | |
|---|---|---|---|---|---|---|---|---|---|---|---|---|
| | | c | c + 2 | | c | c + 2 | | z | z + 2 | | z | z + 2 |
| D | 1 | 133.06 | 67.03 | 1 | — | — | 15 | — | — | 15 | — | — |
| A | 2 | 204.10 | 102.55 | 2 | — | — | 14 | 2643.06 | 1322.03 | 14 | — | — |
| E | 3 | 333.14 | 167.07 | 3 | 333.14 | — | 13 | 2572.02 | 1286.52 | 13 | — | — |
| F | 4 | 480.21 | 240.61 | 4 | 480.21 | — | 12 | 2442.98 | 1221.99 | 12 | — | — |
| R | 5 | 636.31 | 318.66 | 5 | 636.31 | — | 11 | 2295.91 | 1148.46 | 11 | — | — |
| H | 6 | 773.37 | 387.19 | 6 | 773.37 | — | 10 | 2139.81 | 1070.41 | 10 | — | — |
| D | 7 | 888.40 | 444.70 | 7 | 888.40 | — | 9 | 2002.75 | 1001.88 | 9 | — | 1001.89 |
| S | 8 | 975.43 | 488.22 | 8 | 975.43 | — | 8 | 1887.73 | 944.37 | 8 | — | — |
| G | 9 | 1032.45 | 516.73 | 9 | 1032.46 | — | 7 | 1800.69 | 900.85 | 7 | — | — |
| Y(947.323) | 10 | 2142.84 | 1071.92 | 10 | — | 1071.92 | 6 | 1743.67 | 872.34 | 6 | — | 872.35 |
| E | 11 | 2271.88 | 1136.44 | 11 | — | 1136.45 | 5 | 633.29 | 317.15 | 5 | 633.29 | — |
| V | 12 | 2370.95 | 1185.98 | 12 | — | 1186.94 | 4 | 504.24 | 252.63 | 4 | 504.24 | — |
| H | 13 | 2508.01 | 1254.51 | 13 | — | 1254.52 | 3 | 405.18 | 203.09 | 3 | 405.18 | — |
| H | 14 | 2645.06 | 1323.04 | 14 | — | — | 2 | 268.12 | 134.56 | 2 | 268.12 | — |
| Q | 15 | — | — | 15 | — | — | 1 | 131.06 | 66.03 | 1 | — | — |

TABLE 1b

Mass spectrometric evidence for the glycan sequence of the Neu5AcHex(Neu5Ac)HexNAc-O-(Tyr10)Abeta1-15 glycopeptide. Theoretical and detected B- and Y-ions generated by Collision induced dissociation (CID) are shown.

| Glycan Sequence | | Theoretical Y-ions | | Detected Y-ions | |
|---|---|---|---|---|---|
| Y-type ions | | Y + 3 | Y + 4 | Y + 3 | Y + 4 |
| Hex(Neu5Ac)HexNAc-Aβ1-15 | 2 | 828.3 | 621.5 | 828.8 | 621.8 |
| HexHexNAc-Aβ1-15 | 2 | 731.3 | 548.7 | 731.5 | 549.1 |
| (Neu5Ac)HexNAc-Aβ1-15 | 1 | 774.3 | 581.0 | 774.7 | — |
| HexNAc-Aβ1-15 | 1 | 677.3 | 508.2 | 677.7 | 508.7 |
| Aβ1-15 | 0 | 609.6 | 457.5 | — | — |

| | | Theoretical B-ions | Detected B-ions |
|---|---|---|---|
| B-type ions | | B + 1 | B + 1 |
| [Neu5AcHexHexNAc + H] | 3 | 657.2 | — |
| [Neu5AcHex + H] | 2 | 454.2 | — |
| [Neu5Ac + H] | 1 | 292.1 | 291.2 |
| [Neu5Ac-$H_2O$ + H] | 1 | 274.1 | 274.0 |

TABLE 2

Identified Abeta glycopeptides from 6E10 immunopurified CSF samples. The glycosylated/unglycosylated spectral intensity ratios for Abeta from AD and controls (C) are shown.

| | | | AD vs C (mean C set to 1)[d] | | | | Mean |
|---|---|---|---|---|---|---|---|
| Glycopeptide[a] | Calc. mass (Da)[b] | MS/MS data[c] | Mean C | StdErr C | Mean AD | StdErr AD | intensity (Log10)[e] |
| Ab1-13 | 1560.6593 | Y | 1.0 | 0.2 | 0.7 | 0.2 | 5.3 |
| Ab1-14 | 1697.7182 | Y | 1.0 | 0.1 | 0.9 | 0.1 | 5.9 |
| Ab1-15 | 1825.7768 | Y | 1.0 | 0.2 | 0.9 | 0.2 | 6.0 |
| SaHHn-Ab1-15 | 2482.0044 | Y | 1.0 | 0.3 | 1.1 | 0.5 | 3.6 |
| $Sa_2$HHn-Ab1-15 | 2773.0999 | Y | 1.0 | 0.1 | 1.4 | 0.1 | 5.1 |
| $LaSa_2$SaHHn-Ab1-15 | 3046.1847 | Y | 1.0 | 0.2 | 1.9 | 0.1 | 4.4 |
| $Sa_3$HHn-Ab1-15 | 3064.1953 | Y | 1.0 | 0.1 | 1.6 | 0.0 | 4.7 |
| Ac-$Sa_3$HHn-Ab1-15 | 3106.2058 | Y | 1.0 | 0.3 | 2.3 | 0.3 | 4.0 |

TABLE 2-continued

Identified Abeta glycopeptides from 6E10 immunopurified CSF samples. The glycosylated/unglycosylated spectral intensity ratios for Abeta from AD and controls (C) are shown.

| Glycopeptide[a] | Calc. mass (Da)[b] | MS/MS data[c] | Mean C | StdErr C | Mean AD | StdErr AD | Mean intensity (Log10)[e] |
|---|---|---|---|---|---|---|---|
| Ab1-16 | 1953.8718 | Y | 1.0 | 0.2 | 1.1 | 0.2 | 5.3 |
| Sa$_2$HHn-Ab1-16 | 2901.1948 | N | 1.0 | 0.2 | 0.6 | 0.1 | <3.0 |
| Sa$_3$HHn-Ab1-16 | 3192.2902 | N | 1.0 | 0.2 | 0.6 | 0.1 | <3.0 |
| Ab1-17 | 2066.9559 | Y | 1.0 | 0.1 | 1.0 | 0.1 | 7.3 |
| SaHHn-Ab1-17 | 2723.1835 | Y | 1.0 | 0.4 | 1.1 | 0.3 | 4.6 |
| Sa$_2$HHn-Ab1-17 | 3014.2789 | Y | 1.0 | 0.1 | 1.2 | 0.1 | 5.8 |
| LaSa$_2$SaHHn-Ab1-17 | 3287.3637 | Y | 1.0 | 0.2 | 1.6 | 0.1 | 4.5 |
| Sa$_3$HHn-Ab1-17 | 3305.3743 | Y | 1.0 | 0.1 | 1.2 | 0.3 | 4.7 |
| Ac-Sa$_3$HHn-Ab1-17 | 3347.3849 | Y | 1.0 | 0.2 | 1.5 | 0.1 | 4.1 |
| Ab1-18 | 2166.0243 | Y | 1.0 | 0.2 | 1.0 | 0.1 | 6.0 |
| SaHHn-Ab1-18 | 2822.2519 | N | 1.0 | 0.2 | 0.9 | 0.2 | 3.3 |
| Sa$_2$HHn-Ab1-18 | 3113.3473 | Y | 1.0 | 0.1 | 1.1 | 0.1 | 4.4 |
| LaSa$_2$SaHHn-Ab1-18 | 3386.4321 | Y | 1.0 | 0.3 | 2.5 | 0.5 | 4.1 |
| Sa$_3$HHn-Ab1-18 | 3404.4427 | Y | 1.0 | 0.2 | 1.4 | 0.4 | 4.5 |
| Ac-Sa$_3$HHn-Ab1-18 | 3446.4533 | Y | 1.0 | 0.2 | 1.3 | 0.5 | 3.2 |
| Ab1-19 | 2313.0927 | Y | 1.0 | 0.1 | 1.2 | 0.1 | 7.3 |
| SaHHn-Ab1-19 | 2969.3203 | N | 1.0 | 0.1 | 1.0 | 0.2 | 4.4 |
| Sa$_2$HHn-Ab1-19 | 3260.4157 | Y | 1.0 | 0.1 | 1.4 | 0.2 | 5.3 |
| LaSa$_2$SaHHn-Ab1-19 | 3533.5006 | Y | 1.0 | 0.4 | 2.5 | 0.6 | 5.2 |
| Sa$_3$HHn-Ab1-19 | 3551.5111 | Y | 1.0 | 0.2 | 1.9 | 0.4 | 5.4 |
| Ac-Sa$_3$HHn-Ab1-19 | 3593.5217 | Y | 1.0 | 0.2 | 1.4 | 0.3 | 4.2 |
| Ab1-20 | 2460.1611 | Y | 1.0 | 0.2 | 1.0 | 0.2 | 5.9 |
| Sa$_2$HHn-Ab1-20 | 3407.4841 | Y | 1.0 | 0.5 | 0.8 | 0.4 | 3.9 |
| Sa$_3$HHn-Ab1-20 | 3698.5795 | N | 1.0 | 0.2 | 0.6 | 0.1 | <3.0 |
| Ab1-28 | 3260.5275 | Y | 1.0 | 0.3 | 0.5 | 0.2 | 6.3 |
| Ab1-30 | 3388.5861 | Y | 1.0 | 0.1 | 1.1 | 0.1 | 6.7 |
| Ab1-33 | 3671.7757 | Y | 1.0 | 0.1 | 1.0 | 0.1 | 7.5 |
| Ab1-34 | 3784.8598 | Y | 1.0 | 0.1 | 0.8 | 0.1 | 7.6 |
| Ab1-37 | 4071.9901 | Y | 1.0 | 0.0 | 1.0 | 0.0 | 7.9 |
| Ab1-38 | 4129.0116 | Y | 1.0 | 0.0 | 1.0 | 0.0 | 8.6 |
| Ab1-39 | 4228.0800 | Y | 1.0 | 0.0 | 1.2 | 0.1 | 7.8 |
| Ab1-40 | 4327.1484 | Y | 1.0 | 0.0 | 1.0 | 0.0 | 8.8 |
| Ab1-42 | 4511.2696 | Y | 1.0 | 0.2 | 0.5 | 0.1 | 6.6 |
| Ab4-15 | 1510.6702 | N | 1.0 | 0.2 | 0.6 | 0.1 | <3.0 |
| Sa$_2$HHn-Ab4-15 | 2457.9932 | Y | 1.0 | 0.4 | 2.2 | 0.9 | 4.0 |
| LaSa$_2$SaHHn-Ab4-15 | 2731.0781 | Y | 1.0 | 0.2 | 0.6 | 0.1 | <3.0 |
| Sa$_3$HHn-Ab4-15 | 2749.0886 | N | 1.0 | 0.2 | 0.6 | 0.1 | <3.0 |
| Ac-Sa$_3$HHn-Ab4-15 | 2791.0992 | N | 1.0 | 0.2 | 0.6 | 0.1 | <3.0 |
| Ab4-17 | 1751.8492 | N | 1.0 | 0.2 | 0.9 | 0.1 | 4.3 |
| SaHHn-Ab4-17 | 2408.0768 | N | 1.0 | 0.1 | 1.3 | 0.3 | 3.5 |
| Sa$_2$HHn-Ab4-17 | 2699.1722 | Y | 1.0 | 0.1 | 1.4 | 0.1 | 5.3 |
| LaSa$_2$SaHHn-Ab4-17 | 2972.2571 | N | 1.0 | 0.2 | 3.0 | 1.0 | 3.5 |
| Sa$_3$HHn-Ab4-17 | 2990.2676 | Y | 1.0 | 0.1 | 2.1 | 0.1 | 4.1 |
| Ac-Sa$_3$HHn-Ab4-17 | 3032.2782 | N | 1.0 | 0.2 | 0.6 | 0.1 | <3.0 |
| Ab(−3-15) | 2183.9812 | N | 1.0 | 0.4 | 0.4 | 0.2 | 3.6 |
| Sa$_2$HHn-Ab(−3-15) | 3131.3043 | Y | 1.0 | 0.1 | 1.1 | 0.2 | 4.4 |
| Sa$_3$HHn-Ab(−3-15) | 3422.3997 | N | 1.0 | 0.2 | 0.7 | 0.1 | 3.1 |
| Ab(−4-15) | 2313.0238 | Y | 1.0 | 0.2 | 0.7 | 0.1 | 5.2 |
| Ab(−5-15) | 2400.0558 | Y | 1.0 | 0.1 | 1.0 | 0.1 | 5.5 |
| Ab(−11-15) | 3113.4518 | Y | 1.0 | 0.2 | 1.0 | 0.1 | 5.9 |
| Ab(−14-15) | 3441.6264 | Y | 1.0 | 0.2 | 1.0 | 0.2 | 5.5 |
| Ab(−21-15) | 4097.9506 | Y | 1.0 | 0.2 | 1.1 | 0.1 | 6.0 |
| Ab(−22-15) | 4211.0347 | Y | 1.0 | 0.2 | 1.4 | 0.2 | 6.4 |
| Ab(−25-15) | 4539.1842 | Y | 1.0 | 0.1 | 1.0 | 0.1 | 7.3 |
| SaHHn-Ab(−25-15) | 5195.4118 | N | 1.0 | 0.1 | 1.0 | 0.2 | 6.3 |
| Sa$_2$HHn-Ab(−25-15) | 5486.5073 | Y | 1.0 | 0.3 | 1.4 | 0.3 | 6.8 |
| (SaHHn)$_3$-Ab(−25-15) | 6507.8671 | Y | 1.0 | 0.2 | 0.7 | 0.2 | 5.8 |
| Ab(−51-15) | 7286.4418 | Y | 1.0 | 0.2 | 1.0 | 0.1 | 6.4 |
| SaHHn-Ab(−51-15) | 7942.6694 | Y | 1.0 | 0.1 | 0.9 | 0.2 | 7.1 |
| Sa$_2$HHn-Ab(−51-15) | 8233.7649 | Y | 1.0 | 0.1 | 0.9 | 0.3 | 6.4 |
| (SaHHn)$_2$-Ab(−51-15) | 8598.8970 | Y | 1.0 | 0.1 | 0.5 | 0.2 | 6.5 |
| Sa$_2$HHnSaHHn-Ab(−51-15) | 8889.9925 | N | 1.0 | 0.4 | 1.0 | 0.5 | 6.0 |
| (SaHHn)$_3$-Ab(−51-15) | 9255.1247 | Y | 1.0 | 0.2 | 0.5 | 0.1 | 7.1 |
| Sa$_2$HHn(SaHHn)$_2$-Ab(−51-15) | 9546.2201 | Y | 1.0 | 0.2 | 0.7 | 0.0 | 6.7 |
| (SaHHn)$_4$-Ab(−51-15) | 9911.3523 | Y | 1.0 | 0.5 | 1.1 | 0.6 | 6.8 |
| Sa$_2$HHn(SaHHn)$_3$-Ab(−51-15) | 10202.4477 | Y | 1.0 | 0.4 | 1.1 | 0.3 | 6.6 |
| (Sa$_2$HHn)$_2$(SaHHn)$_2$-Ab(−51-15) | 10493.5431 | N | 1.0 | 0.3 | 0.8 | 0.2 | 6.0 |
| (SaHHn)$_5$-Ab(−51-15) | 10567.5799 | N | 1.0 | 0.4 | 0.7 | 0.3 | 5.8 |
| Sa$_2$HHn(SaHHn)$_4$-Ab(−51-15) | 10858.6753 | N | 1.0 | 0.3 | 0.6 | 0.1 | 5.3 |
| Ab(−57-15) | 7967.7751 | Y | 1.0 | 0.1 | 1.0 | 0.1 | 7.2 |
| SaHHn-Ab(−57-15) | 8624.0027 | Y | 1.0 | 0.3 | 0.8 | 0.3 | 6.6 |

TABLE 2-continued

Identified Abeta glycopeptides from 6E10 immunopurified CSF samples. The glycosylated/unglycosylated spectral intensity ratios for Abeta from AD and controls (C) are shown.

| Glycopeptide[a] | Calc. mass (Da)[b] | MS/MS data[c] | Mean C | StdErr C | Mean AD | StdErr AD | Mean intensity (Log10)[e] |
|---|---|---|---|---|---|---|---|
| Sa$_2$HHn-Ab(−57-15) | 8915.0982 | Y | 1.0 | 0.1 | 0.8 | 0.2 | 6.8 |
| (SaHHn)$_2$-Ab(−57-15) | 9280.2303 | N | 1.0 | 0.3 | 0.9 | 0.2 | 6.4 |
| Sa$_2$HHnSaHHn-Ab(−57-15) | 9571.3258 | N | 1.0 | 0.2 | 0.8 | 0.1 | 5.8 |
| (SaHHn)$_3$-Ab(−57-15) | 9936.4580 | Y | 1.0 | 0.1 | 0.7 | 0.1 | 6.9 |
| Sa$_2$HHn(SaHHn)$_2$-Ab(−57-15) | 10227.5534 | N | 1.0 | 0.2 | 0.8 | 0.1 | 6.5 |
| (SaHHn)$_4$-Ab(−57-15) | 10592.6856 | Y | 1.0 | 0.3 | 0.6 | 0.2 | 6.9 |
| Sa$_2$HHn(SaHHn)$_3$-Ab(−57-15) | 10883.7810 | N | 1.0 | 0.3 | 0.7 | 0.2 | 6.6 |
| (Sa$_2$HHn)$_2$(SaHHn)$_2$-Ab(−57-15) | 11174.8764 | N | 1.0 | 0.5 | 0.5 | 0.3 | 5.6 |
| (SaHHn)$_5$-Ab(−57-15) | 11248.9132 | N | 1.0 | 0.2 | 75.7 | 40.0 | 6.2 |
| Sa$_2$HHn(SaHHn)$_4$-Ab(−57-15) | 11540.0086 | N | 1.0 | 0.3 | 0.9 | 0.5 | 4.8 |
| Ab(−58-15) | 8054.8072 | Y | 1.0 | 0.2 | 1.2 | 0.1 | 6.7 |
| Ab(−63-15) | 8601.0510 | N | 1.0 | 0.1 | 1.0 | 0.1 | 6.4 |
| SaHHn-Ab(−63-15) | 9257.2786 | N | 1.0 | 0.3 | 1.0 | 0.3 | 6.7 |
| Sa$_2$HHn-Ab(−63-15) | 9548.3741 | N | 1.0 | 0.5 | 1.3 | 0.6 | 6.2 |
| (SaHHn)$_2$-Ab(−63-15) | 9913.5062 | N | 1.0 | 0.6 | 36.2 | 17.5 | 6.3 |
| Sa$_2$HHnSaHHn-Ab(−63-15) | 10204.6017 | Y | 1.0 | 0.3 | 0.9 | 0.1 | 5.9 |
| (SaHHn)$_3$-Ab(−63-15) | 10569.7339 | Y | 1.0 | 0.1 | 0.7 | 0.1 | 7.0 |
| Sa$_2$HHn(SaHHn)$_2$-Ab(−63-15) | 10860.8293 | Y | 1.0 | 0.3 | 0.8 | 0.1 | 6.6 |
| (SaHHn)$_4$-Ab(−63-15) | 11225.9615 | Y | 1.0 | 0.3 | 0.5 | 0.1 | 7.0 |
| Sa$_2$HHn(SaHHn)$_3$-Ab(−63-15) | 11517.0569 | Y | 1.0 | 0.4 | 0.9 | 0.2 | 6.8 |
| (Sa$_2$HHn)$_2$(SaHHn)$_2$-Ab(−63-15) | 11808.1523 | N | 1.0 | 0.3 | 1.0 | 0.4 | 6.1 |
| (SaHHn)$_5$-Ab(−63-15) | 11882.1891 | N | 1.0 | 0.4 | 0.4 | 0.3 | 6.0 |
| Sa$_2$HHn(SaHHn)$_4$-Ab(−63-15) | 12173.2845 | Y | 1.0 | 0.3 | 0.8 | 0.2 | 5.7 |

[a]Ab = Abeta, Sa = Neu5Ac, H = Hex, Hn = HexNAc, LaSa$_2$ = two Neu5Ac linked with lactone formation, Ac = O-acetyl
[b]Monoisotopic mass
[c]Y = MS/MS data obtained, N = MS/MS data not obtained
[d]Normalized values were obtained as described in Example 2.
[e]Log10 values of mean peak intensity of the 13 spectra used in the AD vs. C pilot study. Signal threshold was subjectively set to 1000 (log$_{10}$1000 = 3). Peptides with log10 peak intensity <3.0 in this set have been detected in other spectra

Example 2

In a pilot study, we used CSF samples from AD patients (n=6) and non-AD controls (n=7). We found that the relative abundance of Tyr10 glycosylated Abeta was elevated in AD patients compared to the controls (FIG. 2). We did not see the same increase for the unglycosylated counterparts. For the AD samples the level of Abeta1-42 was lowered and the level of Abeta1-40 was unaffected in accordance with the literature [Blennow, K., Hampel, H., Weiner, M., Zetterberg, H.: Cerebrospinal fluid and plasma biomarkers in Alzheimer disease, Nat Rev Neurol 6, 131-144 (2010)]. The method described in Example 1 was slightly modified to optimize for relative quantitative measurements. For the AD and control study the LTQ-FT was set to acquire full scan mass spectra but no fragmentation events in order to collect as many full scan mass spectra as possible and obtain maximum performance for the semi-quantitative analysis. The spectra were acquired at two different occasions, first 3 AD+3 controls and later 3 AD+4 controls. The DeCyder 2.0 application (GE Healthcare) was used to evaluate the LC-MS full mass data. Output from DeCyder was further processed using in-house developed software. The output from DeCyder was in form of a list containing masses and corresponding intensities, which were exported to Excel and used to assay the compounds of interest, and were further processed to generate the intensity values used in FIG. 2 and in Table 2 (see Example 1). This processing consisted of inserting a threshold value for undetected peaks to avoid exaggerated peak ratios. This value was subjectively chosen somewhat below the intensity value of the lowest detected peak. Further, to minimize influence of acquisition variation all peaks of a certain LC-MS acquisition were normalized to the summed intensity of all the unglycosylated Abeta 1-X peptide peaks within the same LC-MS acquisition since these compounds have shown no or little variation between AD and controls. Finally, the peaks were further normalized so that for each compound the average of the respective controls was set to 1, thus giving direct numbers of the up-/down regulation for AD. This latter normalization was performed within the respective acquisition occasions to avoid long time effects influencing the acquisitions (i.e., for the first acquisition occasion normalization was performed using the average of the three controls belonging to first acquisition, and for the second acquisition normalization was performed using the average of the four controls belonging to the second acquisition).

Example 3

Provided that proper identification of peaks has already been performed with an adequate instrument (such as an fourier transform ion cyclotron resonance (FTICR)) another mass spectrometric method known as multiple reaction monitoring (MRM) can be utilized for analysis of glycosylation of Abeta peptides according to the invention. MRM is presently a sort of "golden standard" for MS quantification purposes and it is typically performed using a triple quadrupole (QqQ) mass spectrometer. Not being a trapping analyzer the dynamic range is rather high. Here the LC system is more likely to be the limiting factor since there is often a trade-off between systems of high loading capacity and high sensitivity. If such instrument is operated in a so-called scanning mode the sensitivity is not very high, but when operating in MRM mode only the compounds of interest at any given time will be monitored. Hence the sensitivity is greatly increased. The instrument is programmed only to monitor specific compounds and only at a small time window when they elute from the LC and are entering the mass analyzer. Although the resolution of a quadrupole is relatively low and the mass accuracy limited these limitations are remedied by setting the first quadrupole to let through only a narrow m/z range (~1 Da). The ions passing through are subjected to CID in the second quadrupole (the collision cell), and then the third is set only to let through another narrow m/z range, now corresponding to one of the fragment ions produced in the collision cell. By selecting a proper precursor-fragment ion combination virtually no interference affects the measurement. Thus, for measurements of Neu5AcHex(Neu5Ac)HexNAc-O-(Tyr10)Abeta1-15 glycopeptide the first quadrupole is set to let through m/z 694 and the second quadrupole is set to measure the signal intensity at m/z 621.8 (see FIG. 1C). Finally, by adding known amounts of standards labeled with stable isotopes (i.e. the same compound but with for example one amino acid containing only $^{13}$C and $^{15}$N instead of the natural isotopic distribution) an absolute quantification can be obtained. An isotopically "normal" compound and the isotopically labeled standard will have the same chemical properties (or at least so close that other errors are far more influencing). By combining MRM with the immunoprecipitation method described in Example 1a number of different isoforms are quantified simultaneously and with extremely high specificity. Furthermore, the problems with relative drift over time will disappear since the measurement is always related to the standard. In summary, the MRM method is sensitive, specific and relatively robust. It allows for good quantitative determination over quite large dynamic range and with no time drift, i.e., measurements performed over an extended period of time can be directly compared. Hence, the combined IP-MRM method for quantification makes it possible to determine Abeta isoform abundance profiles in large clinical sample sets. Such an automated high-sensitivity method for quantification of Abeta isoforms and glycoforms in CSF, is excellent both as a diagnostic method in clinical routine and as a tool to monitor the effect of drug candidates. By selecting four Tyr10-glycosylated Abeta compounds (Neu5AcHex(Neu5Ac)HexNAc-O-(Tyr10)Abeta1-15, Neu5AcNeu5AcHex(Neu5Ac)HexNAc-O-(Tyr10)Abeta1-15, Neu5AcHex(Neu5Ac)HexNAc-O-(Tyr10)Abeta1-17, and O-AcetylNeu5AcNeu5AcHex(Neu5Ac)HexNAc-O-(Tyr10)Abeta1-17) and two unglycosylated Abeta peptides (Abeta1-15 and Abeta1-17) a very sensitive and selective method to distinguish between people having AD and those who do not is achieved.

Using an ultrahigh pressure LC system with 2.1 mm columns and an autoinjector affords for high-throughput measurements. The flow is 100 microliters per minute, which is considerably higher than in examples 1 and 2. However, since the mass spectrometer is setup only to monitor six compounds and their respective stable isotope labeled calibrants, the sensitivity is greatly increased so even less material is needed for a proper measurement. In fact only 0.1 ml of CSF is required for the measurement. The coefficient of variance of the method is determined by multiple injections of the same CSF and is determined to be only 2%. This opens up for large-scale investigations since less time is consumed, the duty cycle is only 15 min (compared to 2 h in Examples 1 and 2), and the amount of CSF is much less demanding (for the measurements in Example 2 an amount of 5 ml per patient was consumed). Being not particularly complex, data output from the LC-MS acquisitions are automatically processed and a diagnostic output is generated.

Using this workflow roughly four hundred samples (AD: n=207, controls: n=198) are analyzed at four different occasions, approximately one month apart. The total analysis time spent is 102 h and the setup time is 6 h (1.5 h per occasion). The results are that 195 of the AD samples and 185 of the control are assigned correctly (based on the assumption that they had been correctly assigned earlier in the clinic). Twelve AD samples are assigned as non-AD and 13 control samples are assigned as AD. This gives a sensitivity of 94% and a specificity of 93%. Hence, this method can be considered both relatively fast, having low sample consumption, and a very useful alternative or complement to the present diagnostic biomarker tools.

Example 4

The sample, which consists of a fixed amount of CSF (1 ml), is subjected to mild oxidation (10 min, 0° C.) with 2 mM periodic acid (Merck, Darmstadt, Germany) in order to convert vicinal hydroxyl groups of sialic acids into aldehyde functional groups. The oxidized CSF sample is subsequently mixed with 0.5 mM Biotin-Hydrazide (Sigma-Aldrich, St. Louis, Mo.) and incubated in darkness at 22° C. for 16 hours in 0.1 M, pH 4.5 acetate (Merck, Darmstadt, Germany) buffer in order to biotinylate oxidized carbohydrates in the CSF sample. Microtiter wells (Nunc, Thermo Fisher Scientific, Denmark) are coated with anti-human amyloid beta (N) 82E1 mouse IgG monoclonal antibody (IBL International GmbH, Hamburg, Germany) by incubating 100 µA of the antibody, diluted in 50 mM, pH 9.6 carbonate (Merck, Darmstadt, Germany) buffer to a concentration of 0.2 ng/µl, in the microtiter wells at 22° C. for 16 hours. The wells are then washed five times with 200 µl of phosphate buffered saline (PBS) (Sigma-Aldrich, St. Louis, Mo.) supplemented with 0.1% (by volume) Tween-20 (Sigma-Aldrich, St. Louis, Mo.) to remove unbound antibodies and now the microtiter wells are immobilized with an antibody which specifically binds the N-terminus end of Abeta peptides. Next, the wells are incubated with 200 µl of PBS+0.1% Tween-20 supplemented with 1% (by weight) bovine serum albumin (BSA), fraction V (Sigma-Aldrich, St. Louis, Mo.) to prevent unspecific binding in downstream steps. The wells are then washed five times with 200 µl of PBS+0.1% Tween-20 to remove excess BSA.

A serial dilution of a standard solution with predetermined concentration of synthetic, C-terminally biotinylated Abeta 1-10 peptide (AnaSpec, Fremont, Calif.) is added to selected microtiter wells and incubated at 22° C. for 2 hours to allow the antibody to bind the standard. For the CSF sample, now containing biotin-labeled glycoconjugates, 200 µl is added to the wells and incubated for at 22° C. for 2 hours to allow the antibody to specifically bind Abeta peptides in the CSF sample. The wells are then washed five times with 200 µl of PBS+0.1% Tween-20 to remove unspecific binding and now Abeta peptides, together with biotin-labeled Abeta glycopeptides, are immobilized in the microtiter wells through the specific interaction of the N-terminal end of the Abeta sequence with the anti-human amyloid beta (N) 82E1 mouse IgG monoclonal antibody. Next, peroxidase conjugated streptavidin (Calbiochem, Merck, Darmstadt, Germany) is added to the microtiter wells and incubated at 22° C. for 2 hours to allow the streptavidin to react with the biotinylated Abeta peptide standard and with the biotin molecules covalently attached to the sialylated glycans on Tyr10 residues of Abeta glycopeptides in the CSF sample. The wells are then washed five times with 200 µl of PBS+0.1% Tween-20 to remove unbound peroxidase conjugated streptavidin. For specific detection of biotinylated Abeta peptide standard and biotinylated Abeta glycopeptides in CSF, 100 μl of peroxidase substrate 3,3',5,5' tetramethylbenzidine (TMB) (Sigma-Aldrich, St. Louis, Mo.) is added to the microtiter wells and the reaction is allowed to proceed for 10 min. The peroxidase-TMB reaction is terminated by the addition of 100 μl of 0.5M $H_2SO_4$ (Merck, Darmstadt, Germany). The signal output generated by the peroxidase-TMB reaction is optically read at 450 nm using iEMS Reader MF (Labsystems, Helsinki, Finland) and designated in absorbance units. The signal output generated by each point in the serial dilution of synthetic, C-terminally biotinylated Abeta peptide is plotted against its predetermined concentration to generate a standard curve. The standard curve is subsequently used to determine the quantity of Tyr10 glycosylated Abeta peptides in the CSF sample by correlating the signal output generated in the microtiter wells incubated with the CSF sample to the standard curve obtained from the synthetic, C-terminally biotinylated Abeta peptide standard.

The specificity of the anti-human amyloid beta (N) 82E1 mouse IgG monoclonal antibody, directed against the N-terminal end of Abeta peptides (Horikoshi et al., (2004) Biochem Biophys Res Commun. 319(3):733-7) ensures that only beta-secretase cleaved APP peptides will be immobilized in the wells, i.e. peptides with a free Asp-1 residue such as the Abeta 1-15 (DAEFRHDSGYEVHHQ) (SEQ ID NO. 2) sequence. Although sialylated N-linked glycans at asparagine residues and sialylated O-linked glycans at serine and threonine residues are also chemically modified with biotin using this approach, these biotinylated glycoconjugates will be removed from the microtiter wells by the wash procedures due to their lack of specific interaction with the anti-human amyloid beta (N) 82E1 mouse IgG monoclonal antibody. Thus, the signal output generated in the microtiter wells incubated with the CSF sample will not be dependent on sialylated glycans attached to asparagine, serine or threonine residues in the APP sequence or on any other glycoproteins in the CSF sample. The immobilization of biotinylated Abeta glycopeptides through the specific interaction with the anti-human amyloid beta (N) 82E1 mouse IgG monoclonal antibody will ensure that only the level of Tyr10 glycosylated Abeta glycopeptides in the CSF sample is assayed using this approach. The concentration of Tyr10 glycosylated Abeta glycopeptides in CSF samples from healthy patients sets a threshold value, which is used to differentiate AD patients from healthy patients. The concentrations of Tyr10 glycosylated Abeta glycopeptides in CSF samples from AD and healthy patients are compared and the results display an increase of Tyr10 glycosylated Abeta glycopeptides in CSF samples from AD patients. This increase above the threshold value is used as an indicator for the progression of AD.

Example 4b

An ELISA kit to measure glycosylated Abeta. The anti-human amyloid beta (N) 82E1 mouse IgG monoclonal antibody (IBL International GmbH, Hamburg, Germany) is coated in microtiter wells via binding to Sheep anti Mouse IgM pre-coated microtiter plates. The sample, which consists of a fixed amount of CSF (1 ml) is added. The wells are then washed five times with 200 μA of phosphate buffered saline (PBS) (Sigma-Aldrich, St. Louis, Mo.) supplemented with 0.1% (by volume) Tween-20 (Sigma-Aldrich, St. Louis, Mo.) to remove unbound protein. Next, an antibody recognizing the Neu5Ac(alpha2,8)Neu5Ac epitope that is present on Tyr10 glycosylated Abeta peptides is added. The antibody has been tagged with biotin before it is added and incubated for 1 h. An example of such an antibody is Antibody GD3, Clone: S2-566, Mouse IgM. The Anti GD3 antibody has been biotinylated by reaction with biotin succinimidyl ester (Pierce) at pH 8 borat buffer and then desalted by a PD-10 Sephadex column (GE Healthcare). The microtiter wells are then washed with 200 μl of phosphate buffered saline (PBS) (Sigma-Aldrich, St. Louis, Mo.) supplemented with 0.1% (by volume) Tween-20 (Sigma-Aldrich, St. Louis, Mo.) to remove unbound antibody. Next, peroxidase conjugated streptavidin (Calbiochem, Merck, Darmstadt, Germany) is added to the microtiter wells and incubated at 22° C. for 2 hours to allow the streptavidin to react with the biotinylated antibody attached to the sialylated glycans on Tyr10 residues of Abeta glycopeptides in the CSF sample. The wells are then washed five times with 200 μl of PBS+0.1% Tween-20 to remove unbound peroxidase conjugated streptavidin. For specific detection of Neu5Ac2alpha8Neu5Ac, 100 μl of peroxidase substrate 3,3',5,5' tetramethylbenzidine (TMB) (Sigma-Aldrich, St. Louis, Mo.) is added to the microtiter wells and the reaction is allowed to proceed for 10 min. The peroxidase-TMB reaction is terminated by the addition of 100 μl of 0.5M $H_2SO_4$ (Merck, Darmstadt, Germany). The signal output generated by the peroxidase-TMB reaction is optically read at 450 nm using iEMS Reader MF (Labsystems, Helsinki, Finland) and designated in absorbance units.

The concentration of Tyr10 glycosylated Abeta glycopeptides in CSF samples is measured as is described in Example 4. Furthermore, the concentration of unglycosylated Abeta peptides is also determined using an antibody raised against an unglycosylated Abeta peptide DSGYEVH (SEQ ID NO 7) The absolute and/or relative concentration of glycosylated versus unglycosylated Abeta peptides is compared to a threshold value, which is used to differentiate AD patients from healthy patients.

Example 4C

In order to detect the presence of Abeta 1-X glycopeptides, with Tyr10 (Abeta numbering) being the glycosylation, in a body fluid, a sandwich-based immunoassay is developed. Immobilization of a suitable antibody onto a substrate is combined with suspended antibody-modified lipid vesicles (liposomes). The substrate-immobilized and liposome-bound antibodies may be directed to different epitopes on Abeta 1-X glycopeptides. The presence of Abeta 1-X glycopeptides in the sample solution, (CSF), results in binding of the antibody-modified liposomes to the substrates. The lipsomes could further be modified with one or several chemical elements capable of emitting light in response to external activation, for example optical, electrical or mechanical. Examples include peroxidases, fluorescent dye. Since (i) the emitted signal from a single lipid vesicle can be imaged using a suitable detector, for example a camera, and since (ii) a single Abeta 1-X glycopeptides is sufficient to bind a single liposome to the substrate, the presence of single Abeta 1-X glycopeptides can be detected. Under diffusion limited binding conditions, the detection limit is around 1 to 100 fM within 24 hours. The concentration of Abeta 1-X glycopeptides is determined from the rate by which liposomes bind to the substrate.

Example 5

In order to stop the progression of or even reverse the pathology of AD a nontoxic dose of a mixture of N-acetylhexosamines (N-acetylGalNAc, N-acetylGlcNAc and N-acetylManNAc, 1:1:1 by weight) is given orally. Typically one dose corresponds to 1-10 g, depending on body mass (100-150 mg/kg body weight), the mixture is given 3 times daily. The effect of the treatment is measured with the previously mentioned MRM technique where increased concentrations of Tyr10 glycosylated peptides of the Abeta1-X series, i.e. (Neu5AcHex(Neu5Ac)HexNAc-O-(Tyr10) Abeta1-15, Neu5AcNeu5AcHex(Neu5Ac)HexNAc-O-(Tyr10)Abeta1-15, Neu5AcHex(Neu5Ac)HexNAc-O-(Tyr10)Abeta1-17, and O-AcetylNeu5AcNeu5AcHex(Neu5Ac)HexNAc-O-(Tyr10)Abeta1-17) versus two unglycosylated Abeta peptides (Abeta1-15 and Abeta1-17), is observed in consecutive CSF samples from a series of patients. The relative increase, versus control patients on placebo treatment, is measured as the increased proportion of glycosylated Abeta peptides versus unglycosylated Abeta peptides normalized to the total concentration of unglycosylated Abeta peptides in CSF. The absolute concentrations of unglycosylated peptides are obtained by the use of isotopically labeled but otherwise identical Abeta peptides added as internal standards, i.e. before purification. Assuming that the purification, chromatographic separation and mass spectrometric ionisation of glycosylated and unglycosylated Abeta peptides are the same the absolute concentrations of glycosylated Abeta peptides is calculated (pmol/L). The daily amounts of the administered monosaccharides are adjusted to the concentrations measured in body fluids and optimized for each patient. The oral administration is continued until any major adverse side effects appear or the treated patient or her legal adviser prefers to stop the therapy. In a typical case of AD the therapy is measurable after about 3 weeks as major changes in glycopeptide distribution in CSF and blood are observed. The cognitive impairment is improved within 3 to 6 months depending on how long the symptoms were established before therapy was introduced and how significant the symptoms were at the start of therapy. Not all patients respond well to therapy depending on the heterogeneity of the AD group of diseases.

The invention claimed is:

1. An in vitro method for diagnosing or prognosing Alzheimer's disease in a subject, or determining whether a subject is at increased risk of developing Alzheimer's disease, comprising the steps of:
   a) obtaining a sample from the subject;
   b) enriching for Abeta peptides in the sample;
   c) separating the Abeta peptides of step b) using liquid chromatography;
   d) identifying Abeta peptide fragments by mass spectrometry;
   e) measuring the level of O-linked glycosylation at Tyr10 of the Abeta peptides; and
   f) utilizing information on the level of O-linked glycosylation at Tyr10 of the Abeta peptides in the sample as compared to a reference value representing a known disease or health status to diagnose or prognose Alzheimer's disease in the subject, or to determine whether there is an increased risk of Alzheimer's disease in the subject.

2. The method according to claim 1, wherein step e) further comprises determining the amount of Abeta peptide with O-linked Tyr10 glycosylation relative to unglycosylated Abeta peptide.

3. The method according to claim 1, wherein the method further comprises determining the amount of unglycosylated Abeta peptide relative to the total amount of Abeta peptide for indirect determination of Tyr10 glycosylated Abeta amount.

4. The method according to claim 1, wherein said sample is selected from the group consisting of cerebrospinal fluid, serum, urine, whole blood, lymphatic fluid, plasma, saliva, cells, tissue, and material secreted by cells or tissues cultured in vitro.

5. The method according to claim 1, wherein the peaks have been previously identified using mass spectrometry and mass spectrometry is performed in Multiple Recognition Mode.

6. The method according to claim 5, wherein the Multiple Recognition Mode comprises three quadrupole settings comprising:
   a. a first quadrupole set to let through a narrow m/z range of about 1 Dalton;
   b. a second quadrupole set so that ions are subjected to Collision Induced Dissociation to produce fragment ions; and
   c. a third quadrupole set to let through a narrow m/z range corresponding to one of the fragment ions produced in Collision Induced Dissociation.

7. The method according to claim 1, wherein a Tyr10-glycosylated Abeta compound selected from the group consisting of Neu5AcHex(Neu5Ac)HexNAc-O-(Tyr10)Abeta1-15, Neu5AcNeu5AcHex(Neu5Ac)HexNAc-O-(Tyr10)Abeta1-15, Neu5AcHex(Neu5Ac)HexNAc-O-(Tyr10)Abeta1-17, and O-AcetylNeu5AcNeu5AcHex(Neu5Ac)HexNAc-O-(Tyr10)Abeta1-17 is detected.

8. The method according to claim 5, wherein a Tyr10-glycosylated Abeta compound selected from the group consisting of Neu5AcHex(Neu5Ac)HexNAc-O-(Tyr10)Abeta1-15, Neu5AcNeu5AcHex(Neu5Ac)HexNAc-O-(Tyr10)Abeta1-15, Neu5AcHex(Neu5Ac)HexNAc-O-(Tyr10)Abeta1-17, and O-AcetylNeu5AcNeu5AcHex(Neu5Ac)HexNAc-O-(Tyr10)Abeta1-17 is detected.

9. The method according to claim 6, wherein a Tyr10-glycosylated Abeta compound selected from the group consisting of Neu5AcHex(Neu5Ac)HexNAc-O-(Tyr10)Abeta1-15, Neu5AcNeu5AcHex(Neu5Ac)HexNAc-O-(Tyr10)Abeta1-15, Neu5AcHex(Neu5Ac)HexNAc-O-(Tyr10)Abeta1-17, and O-AcetylNeu5AcNeu5AcHex(Neu5Ac)HexNAc-O-(Tyr10)Abeta1-17 is detected.

\* \* \* \* \*